(12) United States Patent
Kath et al.

(10) Patent No.: US 7,332,493 B2
(45) Date of Patent: Feb. 19, 2008

(54) SUBSTITUTED BICYCLIC DERIVATIVES FOR THE TREATMENT OF ABNORMAL CELL GROWTH

(75) Inventors: John Charles Kath, Waterford, CT (US); Joel Morris, East Lyme, CT (US); Samit Kumar Bhattacharya, Groton, CT (US)

(73) Assignee: OSI Pharmaceuticals, New York, NY (US)

( * ) Notice: Subject to any disclaimer, the term of this patent is extended or adjusted under 35 U.S.C. 154(b) by 501 days.

(21) Appl. No.: 11/079,648

(22) Filed: Mar. 14, 2005

(65) Prior Publication Data

US 2005/0159435 A1 Jul. 21, 2005

Related U.S. Application Data

(62) Division of application No. 09/883,752, filed on Jun. 18, 2001, now Pat. No. 6,890,924.

(60) Provisional application No. 60/213,136, filed on Jun. 20, 2000.

(51) Int. Cl.
| | |
|---|---|
| A61K 31/517 | (2006.01) |
| C07D 239/84 | (2006.01) |
| C07D 401/12 | (2006.01) |
| C07D 403/12 | (2006.01) |
| C07D 417/12 | (2006.01) |
| A61K 31/538 | (2006.01) |
| C07D 413/12 | (2006.01) |

(52) U.S. Cl. ............................ 514/252.02; 514/234.5; 514/266.2; 514/266.21; 514/266.23; 544/116; 544/238; 544/283; 544/284

(58) Field of Classification Search ............ 514/234.5, 514/266.2, 266.21, 266.23, 252.02; 544/116, 544/238, 283, 284
See application file for complete search history.

(56) References Cited

U.S. PATENT DOCUMENTS

| | | | | | |
|---|---|---|---|---|---|
| 5,821,246 | A | * | 10/1998 | Brown et al. | 514/252.17 |
| 5,955,464 | A | * | 9/1999 | Barker | 514/233.8 |
| 6,127,374 | A | * | 10/2000 | Bridges | 514/217.06 |
| 6,284,764 | B1 | * | 9/2001 | Kath et al. | 514/266.2 |
| 6,465,449 | B1 | * | 10/2002 | Kath et al. | 514/183 |
| 6,890,924 | B2 | * | 5/2005 | Kath et al. | 514/234.5 |

* cited by examiner

*Primary Examiner*—James O. Wilson
*Assistant Examiner*—Tamthom N Truong
(74) *Attorney, Agent, or Firm*—Keith D. Hutchinson; Bryan C. Zielinski

(57) ABSTRACT

The invention relates to compounds of the formula 1

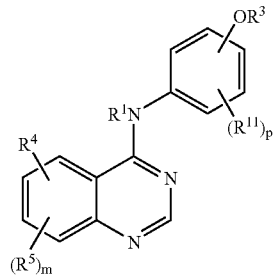

and to pharmaceutically acceptable salts, prodrugs and solvates thereof, wherein $R^1$, $R^3$, $R^4$, $R^5$, $R^{11}$, m and p are as defined herein. The invention also relates to methods of treating abnormal cell growth in mammals by administering the compounds of formula 1 and to pharmaceutical compositions for treating such disorders which contain the compounds of formula 1. The invention also relates to methods of preparing the compounds of formula 1.

11 Claims, No Drawings

SUBSTITUTED BICYCLIC DERIVATIVES FOR THE TREATMENT OF ABNORMAL CELL GROWTH

CROSS-REFERENCE TO RELATED APPLICATION

This is a division of application Ser. No. 09/883,752 filed Jun. 18, 2001, now U.S. Pat. No. 6,890,924, issued May 10, 2005, which claims the benefit of U.S. Provisional Application No. 60/213,136, filed Jun. 20, 2000, both of which are incorporated herein by reference.

This U.S. patent application claims priority from and the benefit of U.S. Provisional Patent Application No. 60/213,136, filed Jun. 20, 2000.

BACKGROUND OF THE INVENTION

This invention relates to novel bicyclic derivatives that are useful in the treatment of abnormal cell growth, such as cancer, in mammals. This invention also relates to a method of using such compounds in the treatment of abnormal cell growth in mammals, especially humans, and to pharmaceutical compositions containing such compounds.

It is known that a cell may become cancerous by virtue of the transformation of a portion of its DNA into an oncogene (i.e., a gene which, on activation, leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. Other receptor tyrosine kinases include c-erbB-2, c-met, tie-2, PDGFr, FGFr, and VEGFR. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR), which possesses tyrosine kinase activity, is mutated and/or overexpressed in many human cancers such as brain, lung, squamous cell, bladder, gastric, breast, head and neck, oesophageal, gynecological and thyroid tumors.

Accordingly, it has been recognized that inhibitors of receptor tyrosine kinases are useful as selective inhibitors of the growth of mammalian cancer cells. For example, erbstatin, a tyrosine kinase inhibitor, selectively attenuates the growth in athymic nude mice of a transplanted human mammary carcinoma which expresses epidermal growth factor receptor tyrosine kinase (EGFR) but is without effect on the growth of another carcinoma which does not express the EGF receptor. Thus, the compounds of the present invention, which are selective inhibitors of certain receptor tyrosine kinases, are useful in the treatment of abnormal cell growth, in particular cancer, in mammals. In addition to receptor tyrosine kianses, the compounds of the present invention can also display inhibitory activity against a variety of other non-receptor tyrosine kinases (eg: lck, src, abl) or serine/threonine kinases (e.g.: cyclin dependent kinases).

Various other compounds, such as styrene derivatives, have also been shown to possess tyrosine kinase inhibitory properties. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are U.S. patent application Ser. No. 09/488,350 (filed Jan. 20, 2000) and Ser. No. 09/488,378 (filed Jan. 20, 2000), both of which are incorporated herein by reference in their entirety.

SUMMARY OF THE INVENTION

The present invention relates to compounds of the formula 1

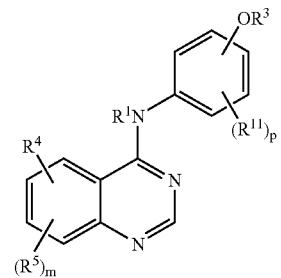

and to pharmaceutically acceptable salts, solvates and prodrugs thereof, wherein:

m is an integer from 0 to 3;

p is an integer from 0 to 4;

each $R^1$ and $R^2$ is independently selected from H and $C_1$-$C_6$ alkyl;

$R^3$ is —$(CR^1R^2)_t$(4 to 10 membered heterocyclic), wherein t is an integer from 0 to 5, said heterocyclic group is optionally fused to a benzene ring or a $C_5$-$C_8$ cycloalkyl group, the —$(CR^1R^2)_t$— moiety of the foregoing $R^3$ group optionally includes a carbon-carbon double or triple bond where t is an integer between 2 and 5, and the foregoing $R^3$ groups, including any optional fused rings referred to above, are optionally substituted by 1 to 5 $R^8$ groups;

$R^4$ is —$(CR^{16}R^{17})_m$—C≡C—$(CR^{16}R^{17})_t R^9$, —$(CR^{16}R^{17})_m$—C=C—$(CR^{16}R^{17})_t$—$R^9$, —$(CR^{16}R^{17})_m$—C≡C—$(CR^{16}R^{17})_k R^{13}$, —$(CR^{16}R^{17})_m$—C=C—$(CR^{16}R^{17})_k R^{13}$, or —$(CR^{16}R^{17})_t R^9$, wherein the attachment point to $R^9$ is through a carbon atom of the $R^9$ group, each k is an integer from 1 to 3, each t is an integer from 0 to 5, and each m is an integer from 0 to 3;

each $R^5$ is independently selected from halo, hydroxy, —$NR^1R^2$, $C_1$-$C_6$ alkyl, trifluoromethyl, $C_1$-$C_6$ alkoxy, trifluoromethoxy, —$NR^6C(O)R^1$, —$C(O)NR^6R^7$, —$SO_2NR^6R^7$, —$NR^6C(O)NR^7R^1$, and —$NR^6C(O)OR^7$;

each $R^6$, $R^{6a}$ and $R^7$ is independently selected from H, $C_1$-$C_6$ alkyl, —$(CR^1R^2)_t(C_6$-$C_{10}$ aryl), and —$(CR^1R^2)_t$(4 to 10 membered heterocyclic), wherein t is an integer from 0 to 5, 1 or 2 ring carbon atoms of the heterocyclic group are optionally substituted with an oxo (=O) moiety, the alkyl, aryl and heterocyclic moieties of the foregoing $R^6$ and $R^7$ groups are optionally substituted with 1 to 3 substituents independently selected from halo, cyano, nitro, —$NR^1R^2$, trifluoromethyl, trifluoromethoxy, $C_1$-$C_6$ alkyl, $C_2$-$C_6$ alkenyl, $C_2$-$C_6$ alkynyl, hydroxy, and $C_1$-$C_6$ alkoxy;

or $R^6$ and $R^7$, or $R^{6a}$ and $R^7$, when attached to a nitrogen atom; (including the same nitrogen atom or two separate nitrogen atoms in proximity to each other through interconection by, for instance, —C(O) or —$SO_2$—), can be taken together to form a 4 to 10 membered heterocyclic ring which may include 1 to 3 additional hetero moieties in addition to the nitrogen to which said $R^6$, $R^{6a}$, and $R^7$ are attached, selected from N, N($R^1$), O, and S, provided two O atoms, two S atoms or an O and S atom are not attached directly to each other;

each $R^8$ is independently selected from oxo (=O), halo, cyano, nitro, trifluoromethoxy, trifluoromethyl, azido, hydroxy, $C_1$-$C_6$ alkoxy, $C_1$-$C_{10}$ alkyl, $C_2$-$C_6$ alkenyl, $C_2$-$C_6$ alkynyl, —$C(O)R^6$, —$C(O)OR^6$, —$OC(O)R^6$, —$NR^6C(O)R^7$, —$NR^6SO_2NR^7R^1$, —$NR^6C(O)NR^1R^7$, —$NR^6C(O)OR^7$, —$C(O)NR^6R^7$, —$NR^6R^7$, —$NR^6OR^7$, —$SO_2NR^6R^7$, —$S(O)_j(C_1$-$C_6$ alkyl) wherein j is an integer from 0 to 2, —$(CR_1R^2)_t(C_6$-$C_{10}$ aryl), —$(CR^1R^2)_t$ (4 to 10 membered heterocyclic), —$(CR^1R^2)_qC(O)(CR^1R^2)_t(C_6$-$C_{10}$ aryl), —$(CR^1R^2)_qC(O)$ $(CR^1R^2)_t$ (4 to 10 membered heterocyclic), —$(CR^1R^2)_qO(CR^1R^2)_q(C_6$-$C_{10}$ aryl), —$(CR^1R^2)_tO$ $(CR^1R^2)_q$ (4 to 10 membered heterocyclic), —$(CR_1R^2)_qS$ $(O)_j(CR^1R^2)_t(C_6$-$C_{10}$ aryl), and —$(CR^1R^2)_qS(O)_j(CR^1R^2)_t$ (4 to 10 membered heterocyclic), wherein j is 0, 1 or 2, q and t are each independently an integer from 0 to 5, 1 or 2 ring carbon atoms of the heterocyclic moieties of the foregoing $R^8$ groups are optionally substituted with an oxo (=O) moiety, and the alkyl, alkenyl, alkynyl, aryl and heterocyclic moieties of the foregoing $R^8$ groups are optionally substituted with 1 to 3 substituents independently selected from halo, cyano, nitro, trifluoromethyl, trifluoromethoxy, azido, —$OR^6$, —$C(O)R^6$, —$C(O)OR^6$, —$OC(O)R^6$, —$NR^6C(O)R^7$, —$C(O)NR^6R^7$, —$NR^6R^7$, —$NR^6OR^7$, $C_1$-$C_6$ alkyl, $C_2$-$C_6$ alkenyl, $C_2$-$C_6$ alkynyl, —$(CR^1R^2)_t(C_6$-$C_{10}$ aryl), and —$(CR^1R^2)_t$(4 to 10 membered heterocyclic), wherein t is an integer from 0 to 5;

$R^9$ is a non-aromatic mono-cyclic ring, a fused or bridged bicyclic ring, or a spirocyclic ring, wherein said ring contains from 3 to 12 carbon atoms in which from 0 to 3 carbon atoms are optionally replaced with a hetero moiety independently selected from N, O, S(O)$_j$ wherein j is an integer from 0 to 2, and —$NR^1$—, provided that two O atoms, two S(O)$_j$ moieties, an O atom and a S(O)$_j$ moiety, an N atom and an S atom, or an N atom and an O atom are not attached directly to each other within said ring, and wherein the carbon atoms of said ring are optionally substituted with 1 or 2 $R^8$ groups;

each $R^{11}$ is independently selected from the substituents provided in the definition of $R^8$, except $R^{11}$ is not oxo (=O);

$R^{12}$ is $R^6$, $OR^6$, —$OC(O)R^6$, —$OC(O)NR^6R^7$, —$OCO_2R^6$, —$S(O)_jR^6$, —$S(O)_jNR^6R^7$, —$NR^6R^7$, —$NR^6C(O)R^7$, —$NR^6SO_2R^7$, —$NR^6C(O)NR^{6a}R^7$, —$NR^6SO_2NR^{6a}R^7$, —$NR^6CO_2R^7$, CN, —$C(O)R^6$, or halo, wherein j is an integer from 0 to 2;

$R^{13}$ is —$NR^1R^{14}$ or —$OR^{14}$;

$R^{14}$ is H, $R^{15}$, —$C(O)R^{15}$, —$SO_2R^{15}$, —$C(O)NR^{15}R^7$, —$SO_2NR^{15}R^7$, or —$CO_2R^{15}$;

$R^{15}$ is $R^{18}$, —$(CR^1R^2)_t(C_6$-$C_{10}$ aryl), —$(CR^1R^2)_t$ (4 to 10 membered heterocyclic), wherein t is an integer from 0 to 5, 1 or 2 ring carbon atoms of the heterocyclic group are optionally substituted with an oxo (=O) moiety, and the aryl and heterocyclic moieties of the foregoing. $R^{15}$ groups are optionally substituted with 1 to 3 $R^8$ substituents;

each $R^{16}$ and $R^{17}$ is independently selected from H, $C_1$-$C_6$ alkyl, and —$CH_2OH$, or $R^{16}$ and $R^{17}$ are taken together as —$CH_2CH_2$— or —$CH_2CH_2CH_2$—;

$R^{18}$ is $C_1$-$C_6$ alkyl wherein each carbon not bound to a N or O atom, or to S(O), wherein j is an integer from 0 to 2, is optionally substituted with $R^{12}$;

and wherein any of the above-mentioned substituents comprising a $CH_3$ (methyl), $CH_2$ (methylene), or CH (methine) group, which is not attached to a halogeno, SO or $SO_2$ group or to a N, O or S atom, is optionally subsituted with a group selected from hydroxy, halo, $C_1$-$C_4$ alkyl, $C_1$-$C_4$ alkoxy and —$NR^1R^2$.

In a specific embodiment of the present invention, $R^3$ is —$(CR_1R^2)_t$ (4 to 10 membered heterocyclic), wherein t is an integer from 0 to 5; said heterocyclic group is optionally fused to a benzene ring or a $C_5$-$C_8$ cycloalkyl group, and the foregoing $R^3$ groups, including any optional fused rings referred to above, are optionally substituted by 1 to 3 $R^8$ groups.

Other specific embodiments of the compounds of formula 1 include those wherein $R^3$ is —$(CR^1R^2)_t$ (4 to 10 membered heterocyclic), wherein t is an integer from 0 to 5, and the foregoing $R^3$ groups are optionally substituted by 1 to 3 $R^8$ groups.

Other specific embodiments of the compounds of formula 1 include those wherein $R^3$ is selected from

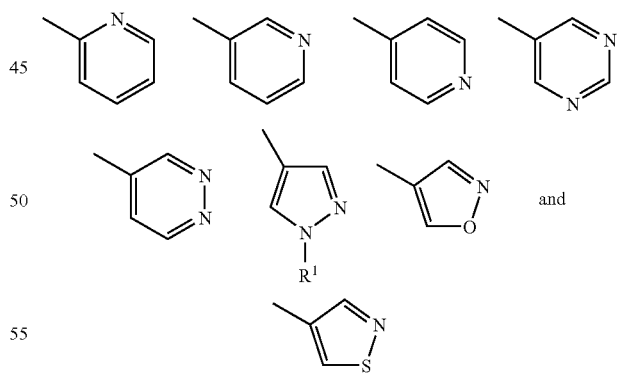

wherein the foregoing $R^3$ groups are optionally substituted by 1 to 3 $R^8$ groups.

Other specific embodiments of the compounds of formula 1 include those wherein $R^3$ is pyridin-3-yl optionally substituted by 1 to 3 $R^8$ groups.

Other specific embodiments of the compounds of formula 1 include those wherein, the following structural portion of the compound of formula 1

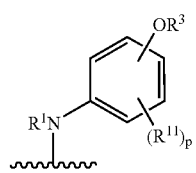

is selected from the group consisting of
3-Methyl-4-(pyridin-2-yloxy)-phenylamino
3-Chloro-4-(pyridin-2-yloxy)-phenylamino
3-Methoxy-4-(pyridin-2-yloxy)-phenylamino
4-(pyridin-2-yloxy)-phenylamino
2-Methyl-4-(pyridin-2-yloxy)-phenylamino,
2-Methoxy-4-(pyridin-2-yloxy)-phenylamine
3-Chloro-4-(6-methyl-pyridin-2-yloxy)-phenylamino
3-Methoxy-4-(6-methyl-pyridin-2-yloxy)-phenylamino
3-Methyl-4-(6-methyl-pyridin-2-yloxy)-phenylamino
2-Methoxy-4-(6-methyl-pyridin-2-yloxy)-phenylamino
2-Methyl-4-(6-methyl-pyridin-2-yloxy)-phenylamino
4-(6-methyl-pyridin-2-yloxy)-phenylamino
3-Methoxy-4-(2-methyl-pyridin-3-yloxy)-phenylamino
3-Methyl-4-(2-methyl-pyridin-3-yloxy)-phenylamino
3-Chloro-4-(2-methyl-pyridin-3-yloxy)-phenylamino
2-Methoxy-4-(2-methyl-pyridin-3-yloxy)-phenylamino
2-Methyl-4-(2-methyl-pyridin-3-yloxy)-phenylamino
4-(2-methyl-pyridin-3-yloxy)-phenylamino
3-Methyl-4-(6-methyl-pyridin-3-yloxy)-phenylamino
3-Chloro-4-(6-methyl-pyridin-3-yloxy)-phenylamino
3-Methoxy-4-(6-methyl-pyridin-3-yloxy)-phenylamino
2-Methyl-4-(6-methyl-pyridin-3-yloxy)-phenylamino
2-Methoxy-4-(6-methyl-pyridin-3-yloxy)-phenylamino
4-(6-methyl-pyridin-3-yloxy)-phenylamino
3-Methyl-4-(pyridin-3-yloxy)-phenylamino
3-Chloro-4-(pyridin-3-yloxy)-phenylamino
3-Methoxy-4-(pyridin-3-yloxy)-phenylamino
2-Methyl-4-(pyridin-3-yloxy)-phenylamino
2-Methoxy-(pyridin-3-yloxy)-phenylamino
4-(pyridin-3-yloxy)-phenylamino
3-Methyl-(2-methyl-pyrimidin-5-yloxy)-phenylamino
3-Chloro-4-(p-methyl-pyrimidin-5-yloxy)-phenyl amino
3-Methoxy-4-(2-methyl-pyrimidin-5-yloxy)-phenylamino
2-Methyl-4-(2-methyl-pyrimidin-5-yloxy)-phenylamino
2-Methoxy-4-(2-methyl-pyrimidin-5-yloxy)-phenylamino
4-(2-methyl-pyrimidin-5-yloxy)-phenylamino
3-Methyl-4-(4-methyl-pyrimidin-5-yloxy)-phenylamino
3-Chloro-4-(4-methyl-pyrimidin-5-yloxy)-phenylamino
3-Methoxy-4-(4-methyl-pyrimidin-5-yloxy)-phenylamino
2-Methyl-4-(4-methyl-pyrimidin-5-yloxy)-phenylamino
2-Methoxy-4-(4-methyl-pyrimidin-5-yloxy)-phenylamino
4-(4-methyl-pyrimidin-5-yloxy)-phenylamino
3-Methyl-4-(2-methyl-pyridin-4-yloxy)-phenylamino
3-Chloro-4-(2-methyl-pyridin-4-yloxy)-phenylamino
3-Methoxy-4-(2-methyl-pyridin-4-yloxy)-phenylamino
2-Methyl-4-(2-methyl-pyridin-4-yloxy)-phenylamino
2-Methoxy-4-(2-methyl-pyridin-4-yloxy)-phenylamino
4-(2-methyl-pyridin-4-yloxy)-phenylamino
3-Methyl-4-(pyridin-4-yloxy)-phenylamino
3-Chloro-4-(pyridin-4-yloxy)-phenylamino
3-Methoxy-4-(pyridin-4-yloxy)-phenylamino
2-Methyl-4-(pyridin-4-yloxy)-phenylamino
2-Methoxy-4-(pyridin-4-yloxy)-phenylamino
4-(pyridin-4-yloxy)-phenylamino
3-Methyl-4-(2-methyl-pyrimidin-4-yloxy)-phenylamino
3-Methoxy-4-(2-methyl-pyrimidin-4-yloxy)-phenylamino
3-Chloro-4-(2-methyl-pyrimidin 4-yloxy)-phenylamino
2-Methyl-4-(2-methyl-pyrimidin-4-yloxy)-phenylamino
2-Methoxy-4-(2-methyl-pyrimidin-4-yloxy)-phenylamino
4-(2-methyl-pyrimidin-4-yloxy)-phenylamino
3-Methyl-4-(6-methyl-pyrimidin-4-yloxy)-phenylamino
3-Methoxy-4-(6-methyl-pyrimidin-4-yloxy)-phenylamino
3-Chloro-4-(6-methyl-pyrimidin-4-yloxy)-phenylamino
2-Methyl-4-(6-methyl-pyrimidin-4-yloxy)-phenylamino
2-Methoxy-4-(6-methyl-pyrimidin-4-yloxy)-phenylamino
4-(6-methyl-pyrimidin-4-yloxy)-phenylamino
3-Methyl-4-(pyrazin-2-yloxy)-phenylamino
3-Methoxy-4-(pyrazin-2-yloxy)-phenylamino
3-Chloro-4-(pyrazin-2-yloxy)-phenylamino
2-Methyl-4-(pyrazin-2-yloxy)-phenylamino
2-Methoxy-4-(pyrazin-2-yloxy)-phenylamino
4-(pyrazin-2-yloxy)-phenylamino,
3-Chloro-4-(3-methyl-pyrazin-2-yloxy)-phenylamino
3-Methoxy-4-(3-methyl-pyrazin-2-yloxy)-phenylamino
3-Methyl-4-(3-methyl-pyrazin-2-yloxy)-phenylamino
2-Methoxy-4-(3-methyl-pyrazin-2-yloxy)-phenylamino
2-Methyl-4-(3-methyl-pyrazin-2-yloxy)-phenylamino
4-(3-methyl-pyrazin-2-yloxy)-phenylamino
3-Chloro-4-(5-methyl-pyrazin-2-yloxy)-phenylamino
3-Methoxy-4-(5-methyl-pyrazin-2-yloxy)-phenylamino
3-Methyl-4-(5-methyl-pyrazin-2-yloxy)-phenylamino
2-Methoxy-4-(5-methyl-pyrazin-2-yloxy)-phenylamino
2-Methyl-4-(5-methyl-pyrazin-2-yloxy)-phenylamino
4-(5-methyl-pyrazin-2-yloxy)-phenylamino
3-Chloro-4-(6-methyl-pyrazin-2-yloxy)-phenylamino
3-Methoxy-4-(6-methyl-pyrazin-2-yloxy)-phenylamino
3-Methyl-4-(6-methyl-pyrazin-2-yloxy)-phenylamino
2-Methoxy-4-(6-methyl-pyrazin-2-yloxy)-phenylamino
2-Methyl-4-(6-methyl-pyrazin-2-yloxy)-phenylamino
4-(6-methyl-pyrazin-2-yloxy)-phenylamino
3-Methyl-(pyridazin-2-yloxy)-phenylamino
3-Chloro-4-(pyridazin-3-yloxy)-phenylamino
3-Methoxy-4-(pyridazin-3-yloxy)-phenylamino
2-Methyl-4-(pyridazin-3-yloxy)-phenylamino
2-Methoxy-4-(pyridazin-3-yloxy)-phenylamino
4-(pyridazin-3-yloxy)-phenylamino
3-Methyl-4-(6-methyl-pyridazin-3-yloxy)-phenylamino
3-Chloro-4-(6-methyl-pyridazin 3-yloxy)-phenylamino
3-Methoxy-4-(6-methyl-pyridazin-3-yloxy)-phenylamino
2-Methoxy-4-(6-methyl-pyridazin-3-yloxy)-phenylamino
2-Methoxy-4-(6-methyl-pyridazin-3-yloxy)-phenylamino
4-(6-methyl-pyridazin-3-yloxy)-phenylamino
3-Methyl-4-(6-methyl-pyridazin-4-yloxy)-phenylamino
3-Chloro-4-(6-methyl-pyridazin-4-yloxy)-phenylamino
3-Methoxy-4-(6-methyl-pyridazin-4-yloxy)-phenylamino
2-Methyl-4-(6-methyl-pyridazin-4-yloxy)-phenylamino
2-Methoxy-4-(6-methyl-pyridazin-4-yloxy)-phenylamino
4-(6-methyl-pyridazin-4-yloxy)-phenylamino
3-Methyl-4-(3-methyl-pyridazin-4-yloxy)-phenylamino
3-Chloro-4-(3-methyl-pyridazin-4-yloxy)-phenylamino
3-Methoxy-4-(3-methyl-pyridazin-4-yloxy)-phenylamino
2-Methyl-4-(3-methyl-pyridazin-4-yloxy)-phenylamino
2-Methoxy-4-(3-methyl-pyridazin-4-yloxy)-phenylamino
4-(6-methyl-pyridazin-4-yloxy)-phenylamino
3-Methyl-4-(pyridazin-4-yloxy)-phenylamino
3-Chloro-4-(pyridazin-4-yloxy)-phenylamino
3-Methoxy-4-(pyridazin-4-yloxy)-phenylamino
2-Methyl-4-(pyridazin-4-yloxy)-phenylamino
2-Methoxy-4-(pyridazin-4-yloxy)-phenylamino
4-(pyridazin-4-yloxy)-phenylamino
3-Chloro-4-(1-methyl-1H-pyrazol-4-yloxy)-phenylamino
3-Methoxy-4-(1-methyl-1H-pyrazol-4-yloxy)-phenylamino
3-Methyl-4-(1-methyl-1H-pyrazol-4-yloxy)-phenylamino 2-Methoxy-4-(1-methyl-1H-pyrazol-4-yloxy)-phenylamino
2-Methyl-4-(1-methyl-1H-pyrazol-4-yloxy)-phenylamino, and
4-(1-methyl-1H pyrazol-4-yloxy)-phenylamino.

Other specific embodiments of the compounds for formula 1 include those wherein $R^4$ is —$(CR^{16}R^{17})_m$—C≡C—$(CR^{16}R^{17})_t R^9$, wherein m is an integer from 0 to 3, and t is an integer from 0 to 5.

Other specific embodiments of the compounds for formula 1 include those wherein $R^4$ is —$(CR^{16}R^{17})_m$—C≡C—$(CR^{16}R^{17})_t R^9$, wherein m is an integer from 0 to 3, and t is an integer from 0 to 5, wherein $R^9$ is selected from 3-piperidinyl and 4-piperidinyl each of which is optionally substituted with 1 or 2 $R^8$ groups.

Other specific embodiments of the compounds for formula 1 include those wherein $R^4$ is —$(CR^{16}R^{17})_m$C=C—$(CR^{16}R^{17})_t$—$R^9$, wherein m is an integer from 0 to 3, and t is an integer from 0 to 5.

Other specific embodiments of the compounds for formula 1 include those wherein $R^4$ is —$(CR^{16}R^{17})_m$—C=C—$(CR^{16}R^{17})_t$—$R^9$, wherein m is an integer from 0 to 3, and t is an integer from 0 to 5, wherein $R^9$ is selected from 3-piperidinyl and 4-piperidinyl (optionally substituted with 1 or 2 $R^8$ groups).

Other specific embodiments of the compounds for formula 1 include those wherein $R^4$ is —$(CR^{16}R^{17})_m$—C≡C—$(CR^{16}R^{17})_k R^{13}$, wherein k is an integer from 1 to 3 and m is an integer from 0 to 3.

Other specific embodiments of the compounds for formula 1 include those wherein $R^4$ is —$(CR^{16}R^{17})_m$—C≡C—$(CR^{16}R^{17})_k R^{13}$, wherein k is an integer from 1 to 3 and m is an integer from 0 to 3, wherein $R^{13}$ is —$NR^1 R^{14}$, wherein $R^{14}$ is selected from —$C(O)R^{15}$, —$SO_2 R^{15}$, and $C(O)NR^{15}R^7$.

Other specific embodiments of the compounds for formula 1 include those Wherein $R^4$ is —$(CR^{16}R^{17})_m$C=C—$(CR^{16}R^{17})_k R^{13}$, wherein k is an integer from 1 to 3 and m is an integer from 0 to 3.

Others specific embodiments of the compounds for formula 1 include those wherein $R^4$ is —$(CR^{16}R^{17})_m$—C=C—$(CR^{16}R^{17})_k R^{13}$, wherein k is an integer from 1 to 3 and m is an integer from 0 to 3, wherein $R^{13}$ is —$NR^1 R^{14}$, wherein $R^{14}$ is selected from —$C(O)R^{15}$, —$SO_2 R^{15}$, and —$C(O)NR^{15}R^7$.

Other specific embodiments of the compounds for formula 1 include those wherein $R^4$ is —$(CR^{16}R^{17})_m$—C≡C—$(CR^{16}R^{17})_k R^{13}$ or —$(CR^{16}R^{17})_m$—C=C—$(CR^{16}R^{17})_k R^{13}$, wherein k is an integer from 1 to 3 and m is an integer from 0 to 3, $R^{13}$ is —$NR^1 R^{14}$ or —$OR^{14}$, $R^{14}$ is $R^{15}$, $R^{15}$ is $R^{18}$, and $R^{18}$ is $C_1$-$C_6$ alkyl optionally substituted by —$OR^6$, —$S(O)_j R^6$, —$NR^6 R^7$, —$NR^6 C(O)R^7$, —$NR^6 SO_2 R^7$, —$NR^6 CO_2 R^7$, CN, —$C(O)R^6$, or halo.

Specific preferred compounds of the: present invention include those selected from the group consisting of:

(±)-[3-Methyl-4-(pyridin-3-yloxy)-phenyl]-(6-piperidin-3-ylethynyl-quinazolin-4-yl)-amine;
2-Methoxy-N-(3-{4-[3-methyl-4-(pyridin-3-yloxy)-phenylamino]-quinazolin-6-yl}-prop-2-ynyl)-acetamide
(±)-[3-Methyl-4-(6-methyl-pyridin-3-yloxy)-phenyl]-(6-piperidin-3-ylethynyl-quinazolin-4-yl)-amine;
2-Methoxy-N-(3-{4-[3-methyl-4-(2-methyl-pyridin-3-yloxy)-phenylamino]-quinazolin-6-yl}-prop-2-ynyl)-acetamide
[3-Methyl-4-(2-methyl-pyridin-3-yloxy)-phenyl]-(6-piperidin-4-ylethynyl-quinazolin-4-yl)-amine
[3-Methyl-4-(6-methyl-pyridin-3-yloxy)-phenyl]-(6-piperidin-4-ylethynyl-quinazolin-4-yl)-amine;
2-Methoxy-N-(3-{4-[3-methyl-4-(6-methyl-pyridin-3-yloxy)-phenylamino]-quinazolin-6-yl}-prop-2-ynyl)-acetamide;
2-Fluoro-N-(3-{4-[3-methyl-4-(6-methyl-pyridin-3-yloxy)-phenylamino]-quinazolin-6-yl}-prop-2-ynyl)-acetamide;
E-2-Methoxy-N-(3-{4-[3-methyl-4-(6-methyl-pyridin-3-yloxy)-phenylamino]-quinazolin-6-yl}-allyl)-acetamide;
[3-Methyl-4-(pyridin-3-yloxy)-phenyl]-(6-piperidin-4-yl-ethynyl-quinazolin-4-yl)-amine;
2-Methoxy-N-(1-{4-[3-methyl-4-(6-methyl-pyridin-3-yloxy)-phenylamino]-quinazolin-6-ylethynyl}-cyclopropyl)-acetamide;
E-N-(3-{4-[3-Chloro-4-(6-methyl-pyridin-3-yloxy)-phenylamino]-quinazolin-6-yl}-allyl)-2-methoxy-acetamide;
N-(3-{4-[3-Chloro-4-(6-methyl-pyridin-3-yloxy)-phenylamino]-quinazolin-6-yl}-prop-2-ynyl)-acetamide;
N-(3-{4-[3-Methyl-4-(6-methyl-pyridin-3-yloxy)-phenylamino]-quinazolin-6-yl}-prop-2-ynyl)-acetamide;
E-N-(3-{4-[3-Chloro-4-(6-methyl-pyridin-3-yloxy)-phenylamino]-quinazolin-6-yl)-allyl)-acetamide;
E-2-Ethoxy-N-(3-{4-[3-methyl-4-(6-methyl-pyridin-3-yloxy-phenylamino]-quinazolin-6-yl}-allyl)-acetamide;
1-Ethyl-3-(3-{4-[3-methyl-4-(6-methyl-pyridin-3-yloxy)-phenylamino]-quinazolin-6-yl}-prop-2-ynyl)-urea;
piperazine-1-carboxylic acid (3-{4-[3-methyl-4-(6-methyl-pyridin-3-yloxy)-phenylamino]-quinazolin-6-yl}-prop-2-ynyl)-amide;
(±)-2-Hydroxymethyl-pyrrolidine-1-carboxylic acid (3-{4-[3-methyl-4-(6-methyl-pyridin-3-yloxy)-phenylamino]-quinazolin-6-yl}-prop-2-ynyl)-amide;
2-Dimethylamino-N-(3-{4-[3-methyl-4-(pyridin-3-yloxy)-phenylamino]-quinazolin-6-yl}-prop-2-ynyl)-acetamide;
E-N-(3-{4-[3-Methyl-4-(6-methyl-pyridin-3-yloxy)-phenylamino]-quinazolin-6-yl}-allyl)-methanesulfonamide;
Isoxazole-5-carboxylic acid (3-{4-[3-methyl-4-(6-methyl-pyridin-3-yloxy)-phenylamino]-quinazolin-6-yl}-prop-2-ynyl)-amide;
1-(1,1-Dimethyl-3-{4-[3-methyl-4-(6-methyl-pyridin-3-yloxy)-phenylamino]-quinazolin-6-yl}-prop-2-ynyl)-3-ethyl-urea;
and the pharmaceutically acceptable salts, prodrugs and solvates of the foregoing compounds.

This invention also relates to a method for the treatment of abnormal cell growth in a mammal, including a human, comprising administering to said mammal an amount of a compound of the formula 1, as defined above, or a pharmaceutically acceptable salt, solvate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system, (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of formula 1, or a pharmaceutically acceptable salt, solvate or prodrug thereof, that is effective in, treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a pharmaceutical composition for the treatment of abnormal cell growth in a mammal, including a human, comprising an amount of a compound of the formula 1, as defined above, or a pharmaceutically acceptable salt, solvate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

The invention also relates to a pharmaceutical composition for the treatment of abnormal cell growth in a mammal, including a human, which comprises an amount of a compound of formula 1, as defined above, or a pharmaceutically acceptable salt, solvate or prodrug thereof, that is effective in treating abnormal cell growth in combination with a pharmaceutically acceptable carrier and an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

This invention also relates to a method for the treatment of a disorder associated with angiogenesis in a mammal, including a human, comprising administering to said mammal an amount of a compound of the formula 1, as defined above, or a pharmaceutically acceptable salt, solvate or prodrug thereof, that is effective in treating said disorder. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

This invention also relates to a method of (and to a pharmaceutical composition for) treating abnormal cell growth in a mammal which comprise an amount of a compound of formula 1, or a pharmaceutically acceptable salt, solvate or prodrug thereof, and an amount of one or more substances selected from anti-angiogenesis agents, signal transduction inhibitors, and antiproliferative agents, which amounts, are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1 in the methods and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds of the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicylo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

3-[4-(4-chloro-phenoxy)-benzenesulfonylamino]-tetrahydro-pyran-3-carboxylic acid hydroxyamide;

(2R,3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1 methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxamide;

3-endo-3-[4-(4-fluoro-phenoxy)-benzenesulfonylamino]-8-oxa-bicyclo[3.2.1]octane-3-carboxylic acid hydroxyamide; and 3-[4-(4-fluoro-phenoxy)-benzenesulfonylamino]-tetrahydro-furan-3-carboxylic acid hydroxyamide;

and pharmaceutically acceptable salts, solvates and prodrugs of said compounds.

The compounds of formula 1, and the pharmaceutically acceptable salts, solvates and prodrugs thereof, can also be used in combination with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447(Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Massachusettes).

VEGF inhibitors, for example SU-5416 and SU-6668 (Sugen Inc. of South San Francisco, Calif., USA), can also be combined with a compound of formula 1. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome pic), and the monoclonal antibodies AR-209 (Aronex Pharmaceuticals Inc. of The Woodlands, Tex., USA) and 2B-1 (Chiron), may be administered in combination with a compound of formula 1. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used with the compounds of the present invention include inhibitors of the enzyme farnesyl protein transferase and inhibitors of the receptor tyrosine kinase PDGFr, including the compounds disclosed and claimed in the following U.S. patent application Ser. No. 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent application 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

A compound of formula 1 may also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present invention include those described in U.S. Provisional Application 60/113,647 (filed Dec. 23, 1998) which is herein incorporated by reference in its entirety.

"Abnormal cell growth", as used herein, unless otherwise indicated, refers to cell growth that is independent of normal regulatory mechanisms (e.g., loss of contact inhibitions). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating", as used herein, unless otherwise indicated, means reversing, alleviating, inhibiting the progress of, or preventing the disorder or condition to which such term applies, or one or more symptoms of such disorder or condition. The term "treatment" as used herein, unless otherwise indicated, refers to the act of treating as 'treating' is defined immediately above.

The term "halo", as used herein, unless otherwise indicated, includes fluoro, chloro; bromo or iodo. Preferred halo groups are fluoro and chloro.

The term "alkyl"; as used herein, unless otherwise indicated, includes saturated monovalent hydrocarbon radicals having straight, cyclic (including mono- or multi-cyclic moieties) or branched moieties. It is understood that for said alkyl group to include cyclic moieties it must contain at least three carbon atoms.

The term "cycloalkyl", as used herein, unless otherwise indicated, includes saturated monovalent hydrocarbon radicals having cyclic (including mono- or multi-cyclic) moieties.

The term "alkenyl", as used herein, unless otherwise indicated, includes alkyl groups, as defined above, having at least one carbon-carbon double bond.

The term "alkynyl", as used herein, unless otherwise indicated, includes alkyl groups, as defined above, having at least one carbon-carbon triple bond.

The term "aryl" as used herein, unless otherwise indicated, includes an organic radical derived from an aromatic hydrocarbon by removal of one hydrogen, such as phenyl or naphthyl.

The term "alkoxy", as used herein, unless otherwise indicated, includes —O-alkyl groups wherein alkyl is as defined above.

The term "4 to 10 membered heterocyclic", as used herein, unless otherwise indicated, includes aromatic and non-aromatic heterocyclic groups containing one or more heteroatoms each selected from O, S and N, wherein each heterocyclic group has from 4 to 10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The term "Me" means methyl, "Et" means ethyl, and "Ac" means acetyl.

In the definition of $X^1$ above, the —$(CR^1R^2)_m$— and $(CR^{16}R^{17})_k$ moieties, and other similar moieties, as indicated above, may vary in their definition of R1, R2, R16 and R17 for each iteration of the subscript (ie, m, k, etc) above 1. Thus, —$(CR^1R^2)_m$— may include —$CH_2C(Me)(Et)$- where m is 2.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare, pharmaceutically acceptable acid addition salts of such basic compounds of are those that form non-toxic acid addition salts, i.e., salts containing pharmacologically acceptable anions, such as the hydrochloride; hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Certain functional groups contained within the compounds of the present invention can be substituted for bioisosteric groups, that is, groups which have similar spatial or electronic requirements to the parent group, but exhibit differing or improved physicochemical or other properties. Suitable examples are well known to those of skill in the art, and include, but are not limited to moieties described in Patini et al., Chem. Rev, 1996, 96, 3147-3176 and references cited therein.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of formula 1 may also exist as tautomers. This invention relates to the use of all such tautomers and mixtures thereof.

The subject invention also includes isotopically-labelled compounds, and the pharmaceutically acceptable salts, solvates and prodrugs thereof, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}$O, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}$H and $^{14}$C are incorporated, are useful in drug and/or substrate tissue distribution assays. Tritiated, i.e., $^{3}$H, and carbon-14, i.e., $^{14}$C, isotopes are particularly preferred for their ease of preparation and detectability. Further, substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating bacterial infections through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

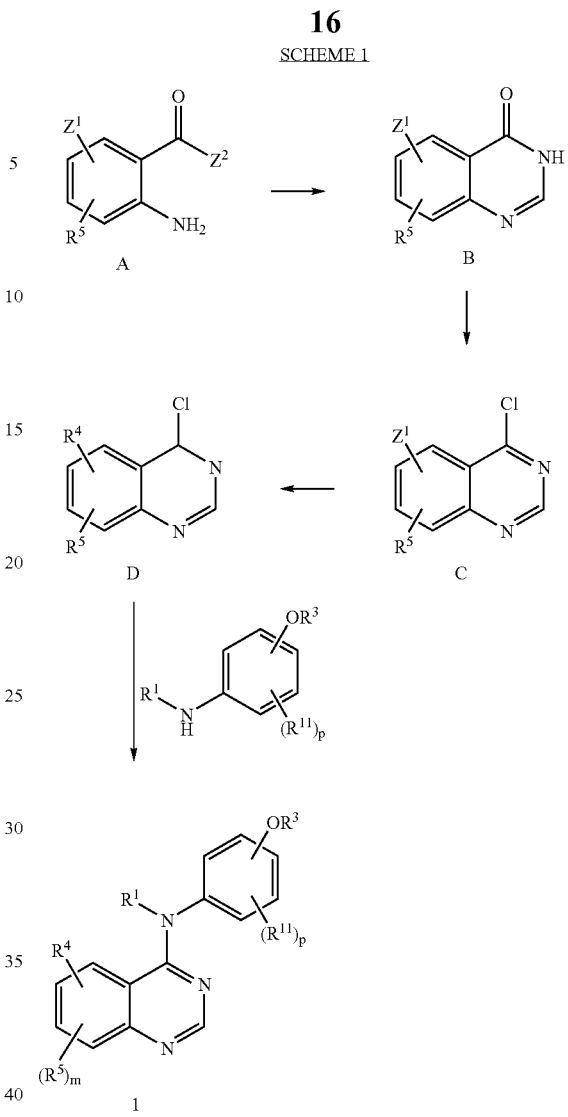

DETAILED DESCRIPTION OF THE INVENTION

General synthetic methods which may be referred to for preparing the compounds of the present invention are provided in U.S. Pat. No. 5,747,498 (issued May 5, 1998), U.S. patent application Ser. No. 08/953,078 (filed Oct. 17, 1997), WO 98/02434 (published Jan. 22, 1998), WO 98/02438 (published Jan. 22, 1998), WO 96/40142 (published Dec. 19, 1996), WO 96/09294 (published Mar. 6, 1996), WO 97/03069 (published Jan. 30, 1997), WO 95/19774 (published Jul. 27, 1995) and WO 97/13771 (published Apr. 17, 1997). Additional procedures are referred to in U.S. patent application Ser. No. 09/488,350 (filed Jan. 20, 2000) and Ser. No. 09/488,378 (filed Jan. 20, 2000). The foregoing patents and patent applications are incorporated herein by reference in their entirety. Certain starting materials may be prepared according to methods familiar to those skilled in the art and certain synthetic modifications may be done according to methods familiar to those skilled in the art. A standard procedure for preparing 6-iodoquinazolinone is provided in Stevenson, T. M., Kazmierczak, F., Leonard, N.

J., J. Org. Chem. 1986, 51, 5, p. 616. Palladium-catalyzed boronic acid couplings are described in Miyaura, N., Yanagi, T., Suzuki, A. Syn. Comm. 1981, 11, 7, p. 513. Palladium catalyzed Heck couplings are described in Heck et. al. Organic Reactions, 1982, 27, 345 or Cabri et. al. in Acc. Chem. Res. 1995, 28, 2. For examples of the palladium catalyzed coupling of terminal alkynes to aryl halides see: Castro et. al. J. Org. Chem. 1963, 28, 3136 or Sonogashira et. al. Synthesis, 1977, 777. Terminal alkyne synthesis may be performed using appropriately substituted/protected aldehydes as described in: Colvin, E. W. J. et. al. Chem. Soc. Perkin Trans. I, 1977, 869; Gilbert, J. C. et. al. J. Org. Chem., 47, 10, 1982; Hauske, J. R. et. al. Tet. Lett., 33, 26, 1992, 3715; Ohira, S. et. al. J. Chem. Soc. Chem. Commun., 9, 1992, 721; Trost, B. M. J. Amer. Chem. Soc., 119, 4, 1997, 698; or Marshall, J. A. et. al. J. Org. Chem., 62, 13, 1997, 4313.

Alternatively terminal alkynes may be prepared by a two step procedure. First, the addition of the lithium anion of TMS (trimethylsilyl)acetylene to an appropriately substituted/protected aldehyde as in: Nakatani, K. et. al. Tetrahedron, 49, 9, 1993, 1901. Subsequent deprotection by base may then be used to isolate the intermediate terminal alkyne as in Malacria, M.; Tetrahedron, 33, 1977, 2813; or White, J. D. et. al. Tet. Lett., 31, 1, 1990, 59.

Starting materials, the synthesis of which is not specifically described above, are either commercially available or can be prepared using methods well known to those of skill in the art.

In each of the reactions discussed or illustrated in the Schemes above, pressure is not critical unless otherwise indicated. Pressures from about 0.5 atmospheres to about 5 atmospheres are generally acceptable, and ambient pressure, i.e., about 1 atmosphere, is preferred as a matter of convenience.

With reference to Scheme 1 above, the compound of formula 1 may be prepared by coupling the compound of formula D wherein $R^4$ and $R^5$ are defined above, with an amine of formula E wherein $R^1$, $R^3$ and $R^{11}$ are as defined above, in an anhydrous solvent, in particular a solvent selected from DMF (N,N-dimethylformamide), DME (ethylene glycol dimethyl ether), DCE (dichloroethane) and t-butanol, and phenol, or a mixture of the foregoing solvents, a temperature within the range of about 50-150° C. for a period ranging from 1 hour to 48 hours. The heteroaryloxyanilines of formula E may be prepared by methods known to those skilled in the art, such as, reduction of the corresponding nitro intermediates. Reduction of aromatic nitro groups may be performed by methods outlined in Brown, R. K., Nelson, N. A. J. Org. Chem. 1954, p. 5149; Yuste, R., Saldana, M, Walls, F., Tet. Lett. 1982, 23, 2, p. 147; or in WO 96/09294, referred to above. Appropriate heteroaryloxy nitrobenzene derivatives may be prepared from halo nitrobenzene precursors by nucleophilic displacement of the halide with an appropriate alcohol as described in Dinsmore, C. J. et. al., Bioorg. Med. Chem. Lett., 7, 10, 1997, 1345; Loupy, A. et. al., Synth. Commun., 20, 18, 1990, 2855; or Brunelle, D. J., Tet. Lett., 25, 32, 1984, 3383. Compounds of formula E in which $R^1$ is a $C_1$-$C_6$ alkyl group may be prepared by reductive amination of the parent aniline with $R^1CH(O)$. The compound of formula D may be prepared by treating a compound of formula C, wherein $Z^1$ is an activating group, such as bromo, iodo, $—N_2$, or $—OTf$ (which is $—OSO_2CF_3$), or the precursor of an activating group such as $NO_2$, $NH_2$ or OH, with a coupling partner, such as a terminal alkyne, terminal alkene, vinyl halide, vinyl stannane, vinylborane, alkyl borane, or an alkyl or alkenyl zinc reagent. The compound of formula C can be prepared by treating a compound of formula B with a chlorinating reagent such as $POCl_3$, $SOCl_2$ or $ClC(O)C(O)Cl/DMF$ in a halogenated solvent at a temperature ranging from about 60° C. to 150° C. for a period ranging from about 2 to 24 hours. Compounds of formula B may be prepared from a compound of formula A wherein $Z^1$ is as described above and $Z^2$ is $NH_2$, $C_1$-$C_6$ alkoxy or OH, according to one or more procedures described in WO 95/19774, referred to above.

Any compound of formula 1 can be converted into another compound of formula 1 by standard manipulations to the $R^4$ group. These methods are known to those skilled in the art and include a) removal of a protecting group by methods outlined in T. W. Greene and P. G. M. Wuts, "Protective Groups in Organic Synthesis", Second Edition, John Wiley and Sons, New York, 1991; b) displacement of a leaving group (halide, mesylate, tosylate, etc) with a primary or secondary amine, thiol or alcohol to form a secondary or tertiary amine, thioether or ether, respectively; c) treatment of phenyl (or substituted phenyl) carbamates with primary of secondary amines to form the corresponding ureas as in Thavonekham, B et. al. Synthesis (1997), 10, p 1189; d) reduction of propargyl or homopropargyl alcohols or N-BOC protected primary amines to the corresponding E-allylic or E-homoallylic derivatives by treatment with sodium bis(2-methoxyethoxy)aluminum hydride (Red-Al) as in Denmark, S. E.; Jones, T. K. J. Org. Chem. (1982) 47, 4595-4597 or van Benthem, R. A. T. M.; Michels, J. J.; Speckamp, W. N. Synlett (1994), 368-370; e) reduction of alkynes to the corresponding Z-alkene derivatives by treatment hydrogen gas and a Pd catalyst as in Tomassy, B. et. al. Synth. Commun. (1998), 28, p 1201 f) treatment of primary and secondary amines with an isocyanate, acid chloride (or other activated carboxylic acid derivative), alkyl/aryl chloroformate or sulfonyl chloride to provide the corresponding urea, amide, carbamate or sulfonamide; g) reductive amination of a primary or secondary amine using $R^1CH(O)$; and h) treatment of alcohols with an isocyanate, acid chloride (or other activated carboxylic acid derivative), alkyl/aryl chloroformate or sulfonyl chloride to provide the corresponding carbamate, ester, carbonate or sulfonic acid ester.

The compounds of the present invention may have asymmetric carbon atoms. Diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of formulas 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula 1 that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula 1. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product. Since a single compound of the present invention may include more than one acidic or basic moieties, the compounds of the present invention may include mono, di or tri-salts in a single compound.

The compounds of the present invention are potent inhibitors of the erbB family of oncogenic and protooncogenic protein tyrosine kinases, in particular erbB2, and thus are all adapted to therapeutic use as antiproliferative agents (e.g., anticancer) in mammals, particularly in humans. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound of the present invention may possess activity against a range of leukemias and lymphoid malignancies.

The compounds of the present invention may also be useful in the treatment of additional disorders in which aberrant expression ligand/receptor interactions or activation or signalling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

The in vitro activity of the compounds of formula 1 may be determined by the following procedure.

The c-erbB2 kinase assay is similar to that described previously in Schrang et. al. Anal. Biochem. 211, 1993, p 233-239. Nunc MaxiSorp 96-well plates are coated by incubation overnight at 37° C. with 100 mL per well of 0.25 mg/mL Poly (Glu, Tyr) 4:1 (PGT) (Sigma Chemical Co., St. Louis, Mo.) in PBS (phosphate buffered saline). Excess PGT is removed by aspiration, and the plate is washed three times with wash buffer (0.1% Tween 20 in PBS). The kinase reaction is performed in 50 mL of 50 mM HEPES (pH 7.5) containing 125 mM sodium chloride, 10 mM magnesium chloride, 0.1 mM sodium orthovanadate, 1 mM ATP, 0.48 mg/mL (24 ng/well) c-erbB2 intracellular domain. The intracellular domain of the erbB2 tyrosine kinase (amino acids 674-1255) is expressed as a GST fusion protein in Baculovirus and purified by binding to and elution from glutathione coated beads. The compound in DMSO (dimethylsulfoxide) is added to give a final DMSO concentration of about 2.5%. Phosphorylation was initiated by addition of ATP (adenosine triphosphate) and proceeded for 6 minutes at room temperature, with constant shaking. The kinase reaction is terminated by aspiration of the reaction mixture and subsequent washing with wash buffer (see above). Phosphorylated PGT is measured by 25 minutes of incubation with 50 mL per well HRP-conjugated PY54 (Oncogene Science Inc. Uniondale, N.Y.) antiphosphotyrosine antibody, diluted to 0.2 mg/mL in blocking buffer (3% BSA and 0.05% Tween 20 in PBS). Antibody is removed by aspiration, and the plate is washed 4 times with wash buffer. The colorimetric signal is developed by addition of TMB Microwell Peroxidase Substrate (Kirkegaard and Perry, Gaithersburg, Md.), 50 mL per well, and stopped by the addition of 0.09 M sulfuric acid, 50 mL per well. Phosphotyrosine is estimated by measurement of absorbance at 450 nm. The signal for controls is typically 0.6-1.2 absorbance units, with essentially no background in wells without the PGT substrate and is proportional to the time of incubation for 10 minutes. Inhibitors were identified by reduction of signal relative to wells without inhibitor and $IC_{50}$ values corresponding to the concentration of compound required for 50% inhibition are determined. The compounds exemplified herein which correspond to formula 1 have IC50 values of <10 μM against erbB2 kinase.

The activity of the compounds of formula 1, in vivo, can be determine by the amount of inhibition of tumor growth by a test compound relative to a control. The tumor growth inhibitory effects of various compounds are measured according to the method of Corbett T. H., et al., "Tumor Induction Relationships in Development of Transplantable Cancers of the Colon in Mice for Chemotherapy Assays, with a Note on Carcinogen Structure", Cancer Res., 35, 2434-2439 (1975) and Corbett T. H., et al., "A Mouse Colon-tumor Model for Experimental Therapy", Cancer Chemother. Rep. (Part 2)", 5, 169-186 (1975), with slight modifications. Tumors are induced in the left flank by subcutaneous (sc) injection of 1-5 million log phase cultured tumor cells (murine FRE-ErbB2 cells or human SK-OV3 ovarian carcinoma cells) suspended in 0.1 ml RPMI 1640 medium. After sufficient time has elapsed for the tumors to become palpable (100-150 mm3 in size/5-6 mm in diameter) the test animals (athymic female mice) are treated with test compound (formulated at a concentration of 10 to 15 mg/ml in 5 Gelucire) by the intraperitoneal (ip) or oral (po) route bf administration once or twice daily for 7 to 10 consecutive days. In order to determine an anti-tumor effect, the tumor is measured in millimeters with a Vernier caliper across two diameters and the tumor size (mm3) is calculated using the formula: Tumor size (mm3)=(length×[width]2)/2, according to the methods of Geran, R. I., et al. "Protocols for Screening Chemical Agents and Natural Products Against Animal Tumors and Other Biological Systems", Third Edition, *Cancer Chemother. Rep.*, 3, 1-104 (1972). Results are expressed as percent inhibition, according to the formula: Inhibition (%)=(TuW$_{control}$−TuW$_{test}$)/TuW$_{control}$×100%. The flank site of tumor implantation provides reproducible dose/response effects for a variety of chemotherapeutic agents, and the method of measurement (tumor diameter) is a reliable method for assessing tumor growth rates.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred antimetabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Where HPLC chromatography is referred to in the preparations and examples below, the general conditions used, unless otherwise indicated, are as follows. The column used is a ZORBAX™ RXC18 column (manufactured by Hewlett Packard) of 150 mm distance and 4.6 mm interior diameter. The samples are run on a Hewlett Packard-1100 system. A gradient solvent method is used running 100 percent ammonium acetate/acetic acid buffer (0.2 M) to 100 percent acetonitrile over 10 minutes. The system then proceeds on a wash cycle with 100 percent acetonitrile for 1.5 minutes and then 100 percent buffer solution for 3 minutes. The flow rate over this period is a constant 3 mL/minute.

In the following examples and preparations, "Et" means ethyl, "AC" means acetyl, "Me" means methyl, "ETOAC" or "ETOAc" means ethyl acetate, "THF" means tetrahydrofuran, and "Bu" means butyl.

Method A: Synthesis of [3-Methyl-4-(pyridin-3-yloxy)-phenyl]-(6-piperidin-4-ylethynyl-quinazolin-4-yl)-amine (1)

4-(4-Chloro-quinazolin-6-ylethynyl)-piperidine-1-carboxylic acid tert-butyl ester: A mixture of 4-ethynyl-piperidine-1-carboxylic acid tert-butyl ester (1.12 g, 5.35 mmol), 4-chloro-6-iodoquinazoline (1.35 g, 4.65 mmol), dichlorobis(triphenylphosphine) palladium(II) (0.16 g, 0.23 mmol), copper(I) iodide (0.044 g, 0.23 mmol), and diisopropylamine (0.47 g, 4.65 mmol) in anhydrous THF (20 mL) was stirred at room temperature under nitrogen for 2 hours. After concentration, the residue was dissolved in $CH_2Cl_2$ (100 mL), washed with aqueous $NH_4Cl$ and brine, dried over sodium sulfate, and concentrated to give the crude product as brown oil. Purification by silica gel column using 20% EtOAc in hexane afforded 1.63 g (94%) of the title compound as a sticky, yellow oil: $^1H$ NMR ($CDCl_3$) δ 1.45 (s, 9H), 1.67-1.75 (m, 2H), 1.87-1.92 (m, 2H), 2.84 (m, 1H), 3.20-3.26 (m, 2H), 3.78 (br d, 2H), 7.88 (dd, 1H), 7.97 (d, 1H), 8.26 (d, 1H), 9.00 (s, 1H).

[3-Methyl-4-(pyridin-3-yloxy)-phenyl]-(6-piperidin-4-yl-ethynyl-quinazolin-4-yl)-amine: 4-(4-Chloro-quinazolin-6-ylethynyl)-piperidine-1-carboxylic acid tert-butyl ester (80 mg, 0.21 mmol) and 3-Methyl-4-(pyridin-3-yloxy)-phenylamine (43 mg, 0.21 mmol) were mixed together in tert-butanol (1 mL) and dichloroethane (1 mL) and heated in a sealed vial at 90° C. for 20 minutes. The reaction was cooled down and HCl (gas) was bubbled through for 5 minutes. EtOAC was then added whereupon yellow precipitation occurred. The precipitate was collected and dried to afford the desired product [3-Methyl-4-(pyridin-3-yloxy)-phenyl]-(6-piperidin-4-ylethynyl-quinazolin-4-yl)-amine as a yellow solid (96 mg, 95%). $^1H$ NMR ($CDCl_3$) δ 2.01 ((m, 2H), 2.22 (m, 2H), 2.35(s, 3H), 3.20 (m, 2H), 3.45(m, 2H), 7.28 (d, 1H, J=8.7 Hz), 7.75(dd, 3H, J1=8.7, J2=8.7 Hz), 8.06 (dd, J=8.7), 8.10 (dd, J1=J2=8.7 Hz), 8.17 (m, 1H), 8.60 (d, 1H, J=5.4 Hz), 8.80 (s, 1H), 8.89 (s, 1H). MS: M+1, 436.6.

Method B: Synthesis of 2-Chloro-N-(3-{4-[3-methyl-4-(pyridin-3-yloxy)-phenylamino]-quinazolin-6-yl}-prop-2-ynyl)-acetamide (2)

2-Chloro-N-[3-(4-chloro-quinazolin-6-yl)-prop-2-ynyl]-acetamide: 2-Chloro-N-prop-2-ynyl-acetamide (385 mg; 2.93 mmol) and 4-chloro-6-iodoquinazoline (850 mg; 1 equiv.) were dissolved in dry THF and diisopropylamine (296 mg; 0.41 mL; 1 equiv.). To this mixture was added 0.04 equivalents of copper iodide (22+mg) and $Pd(PPh_3)_2Cl_2$ (82 mg). The reaction was stirred at room temperature under a nitrogen atmosphere overnight (~20 hrs). The solvent was then removed in vacuo and the residue dissolved in $CH_2Cl_2$. This solution was transferred to a separatory funnel and washed with 1× saturated $NH_4Cl$, brine, dried over $Na_2SO_4$ and the solvent removed in vacuo. The product was purified by silica gel chromatography eluting with 1:1 Hexanes/EtOAc and collecting fractions with an Rf=0.25. 2-Chloro-N-[3-(4-chloro-quinazolin-6-yl)-prop-2-ynyl]-acetamide was obtained as an off white solid (454 mg; 53%). $^1H$ NMR (400 MHz; $CDCl_3$) δ 4.12 (2H, s), 4.40 (2H, d, J=5.2 Hz), 7.91-7.93 (1H, dd, J=2, 6.8 Hz), 8.00 (1H, d, J=8.4 Hz), 8.34 (1H, d, J=1.6 Hz), 9.03 (1H, s). lrms (M+): 294.0, 296.0, 298.1.

2-Chloro-N-(3-{4-[3-methyl-4-(pyridin-3-yloxy)-phenylamino]-quinazolin-6-yl}-prop-2-ynyl)-acetamide: A mixture of 2-Chloro-N-[3-(4-chloro-quinazolin-6-yl)-prop-2-ynyl]-acetamide (0.90 g, 3.05 mmol) and 3-Methyl-4-(pyridin-3-yloxy)-phenylamine (0.61 g, 3.05 mmol) in $^tBuOH$/DCE (5.0/5.0 mL) was refluxed under nitrogen for 40 minutes and concentrated. The residue was dissolved in MeOH (2.0 mL) and added to EtOAc with vigorous stirring to precipitate the HCl salt product as tan solid which was collected by vacuum-filtration, rinsed with EtOAc, and further dried to give 1.24 g (82%) of 2-Chloro-N-(3-{4-[3-methyl-4-(pyridin-3-yloxy)-phenylamino]-quinazolin-6-yl}-prop-2-ynyl)-acetamide: $^1H$ NMR ($CD_3OD$) δ 2.27 (s, 3H), 4.09 (s, 2H), 4.29 (s, 2H), 7.07 (d, 1H), 7.51 (m, 2H), 7.60 (d, 1H), 7.70 (s, 1H), 7.78 (d, 1H), 8.05 (d, 1H), 8.32 (m, 2H), 8.67 (s, 1H), 8.75 (s, 1H); MS m/z (MH$^+$) 458.0.

Method C: Synthesis of 2-Dimethylamino-N-(3-{4-[3-methyl-4-(pyridin-3-yloxy)-phenylamino]-quinazolin-6-yl}-prop-2-ynyl)-acetamide (3)

2-Dimethylamino-N-(3-{4-[3-methyl-4-(pyridin-3-yloxy)-phenylamino]-quinazolin-6-yl}-prop-2-ynyl)-acetamide: To a solution of 2-Chloro-N-(3-{4-[3-methyl-4-(pyridin-3-yloxy)-phenylamino]-quinazolin-6-yl}-prop-2-ynyl)-acetamide (99 mg, 0.20 mmol) in MeOH (5 mL) was added a solution dimethylamine in THF (2 mL, 4.0 mmol). The resulting solution was refluxed under nitrogen for 1 hour. After concentration, the residue was further dried, dissolved in MeOH (1.0 mL), and treated with HCl gas for 3 minutes. The resulting solution was added to EtOAc with vigorous stirring to precipitate the HCl salt product as yellow solid which was collected by vacuum-filtration, rinsed with EtOAc, and further dried to give 110 mg (99%) of the title compound. $^1H$ NMR ($CD_3OD$) δ 2.30 (s, 3H), 2.96 (s, 6H), 4.03 (s, 2H), 4.37 (s, 2H), 7.27 (d, 1H), 7.72 (dt, 1H), 7.81(m, 1H), 7.84 (d, 1H), 8.03 (dd, 1H), 8.06 (d, 1H), 8.13 (dd, 1H), 8.59 (d, 1H), 8.68 (s, 1H), 8.81 (s, 1H), 8.84 (s, 1H); MS m/z (MH$^+$) 467.3.

Method D: Synthesis of 1-(3-{4-[3-Chloro-4-(6-methyl-pyridin-3-yloxy)-phenylamino]-quinazolin-6-yl}-prop-2-ynyl)-3-methyl-urea (4)

1-{4-[3-Chloro-4-(6-methyl-pyridin-3-yloxy)-phenylamino]-quinazolin-6-yl}-prop-2-ynyl)-3-methyl-urea: A mixture of (3-{4-[3-Chloro-4-(6-methyl-pyridin-3-yloxy)phenylamino]-quinazolin-6-yl}-prop-2-ynyl)-carbamic acid phenyl ester (0.1 g, 0.18 mmol) prepared by Method B, methyl amine (2.0M methanol solution, 1 mL, 2 mmol) and DMSO (0.5 mL) was stirred at 80° C. overnight. The solvents were removed under vacuum (GeneVac HT-8) and the residue was re-dissolved in MeOH (~1 mL). HCl gas was bubbled through the solution and EtOAc resulting in precipitation of the desired product. The title compound (80 mg, 90% yield) was obtained by filtration as a yellow solid. $^1HNMR$ (400 MHz, $CD_3OD$) δ 2.72 (3H,s), 2.76 (3H, s), 4.19 (2H, s), 7.49 (1H, d, J=9 Hz), 7.84 (1H, d, J=2 Hz), 7.86 (1H, d, J=2 Hz), 7.92 (1H, d, J=9 Hz), 8.12 (2H, m, J=2 Hz), 8.16 (1H, d, J=2.4 Hz), 8.60 (1H, d, J=3.2 Hz), 8.74 (1H, d, J=1.2 Hz), 8.87 (1H, s). LRMS (M+): 473.0, 475.0, 476.0.

Method E: Synthesis of 3-{4-[3-Methyl-4-(pyridin-3-yloxy)phenylamino]-quinazolin-6-yl}-prop-2-en-1-ol (5)

3-{4-[3-Methyl-4-(pyridin-3-yloxy)-phenylamino]-quinazolin-6-yl}-prop-2-en-1-ol. To a solution of 0.56 g (1.47 mmol) of 3-{4-[3-methyl-4-(pyridin-3-yloxy)-phenylamino]-quinazolin-6-yl}-prop-2-yn-1-ol (prepared by Method B) in 6 mL of dry tetrahydrofuran at 0° C. was added 0.73 mL of a 65% weight toluene solution of sodium bis(2-methoxyethoxy)aluminum hydride (Red-Al, 2.35 mmol) in 1 mL of THF. The reaction was stirred at room temperature for 3 hours. Upon recooling to 0° C. an additional 0.73 mL of the Red-Al solution in 1 mL of THF was added. After stirring for 1 hour at room temperature, the mixture was quenched with the dropwise addition of 10% aqueous potassium carbonate and extracted with ethyl acetate. The organic extracts were dried over sodium sulfate, filtered and evaporated to give 650 mg. Chromatography on 90 g silica gel, eluting with 96:4:0.1 chloroform/methanol/concentrated ammonium hydroxide afforded 268 mg of the title compound. $^1$H NMR (d$_6$ DMSO): δ 9.79 (s, 1), 8.57 (m, 2), 8.35 (m, 2), 8.01 (m, 1), 7.80 (m, 3), 7.41 (m, 1), 7.29 (m, 1), 7.07 (d, J=8.7 Hz, 1), 6.77 (d, J=16.2 Hz, 1), 6.67 (m, 1), 5.04 (t, J=5.6 Hz, 1), 4.23 (m, 2), 2.23 (s, 3).

Method F: Synthesis of [3-Methyl-4-(pyridin-3-yloxy)-phenyl]-[6-(3-morpholin-4-yl-propenyl)-quinazolin-4-yl]-amine (6)

[3-Methyl-4-(pyridin-3-yloxy)-phenyl]-[6-(3-morpholin-4-yl-propenyl)-quinazolin-4-yl]-amine. To a suspension of 0.035 g (0.091 mmol) of 3-{4-[3-methyl-4-(pyridin-3-yloxy) -phenylamino]-quinazolin-6-yl}-prop-2-en-1-ol in 0.5 mL of methylene chloride and 1 mL of ethylene dichloride was added 1 mL of thionyl chloride. The reaction was heated at 100° C. for 1 hour and the solvents were evaporated to provide [6-(3-chloro-propenyl)-quinazolin-4-yl]-[3 methyl-4-(pyridin-3-yloxy)-phenyl]-amine [MS: M$^+$ 403.1] which was dissolved in THF and used directly in the next reaction. To the solution of [6-(3-chloro-propenyl)-quinazolin-4-yl]-[3-methyl-4-(pyridin-3-yloxy)-phenyl]-amine was added 0.10 mL of morpholine and 0.044 mL of triethylamine. The mixture was heated at 85° C. for 16 hours, cooled to room temperature, and partitioned between 10% aqueous potassium carbonate and ethyl acetate. The aqueous layer was further extracted with ethyl acetate and the combined organics were dried and evaporated to yield 57 mg of material. The product was purified on a silica gel prep plate, eluting with 96:4:0.1 chloroform/methanol/concentrated ammonium hydroxide to afford 26 mg of the title compound; $^1$H NMR (CDCl$_3$): δ 8.71 (s, 1), 8.33 (m, 2), 7.94 (s, 1), 7.80 (m, 2), 7.69 (s, 1), 7.58 (m, 1), 7.20 (m, 1), 6.94 (d, J=8.7 Hz, 1), 6.68 (d, J=15.8 Hz, 1), 6.46 (m, 1), 3.79 (m, 4), 3.26(m, 2), 2.63 (m, 4), 2.25 (s, 3).

Method G: Synthesis of E-N-(3-{4-[3-Chloro-4-(6-methyl-pyridin-3-yloxy)-phenylamino]-quinazolin-6-yl}-allyl)-acetamide (7)

E-(3-{4-[3-chloro-4-(6-methyl-pyridin-3-yloxy)-phenylamino]-quinazolin-6-yl}-allyl)-carbamic acid tert-butyl ester: To a solution of 7.53 mL of a 65% weight toluene solution of sodium bis(2-methoxyethoxy)aluminum hydride (Red-Al, 24.2 mmol) in 90 mL of tetrahydrofuran at 0° C. was added 5.0 g of (3-{4-[3-chloro-4-(6-methyl-pyridin-3-yloxy)-phenylamino]-quinazolin-6-yl}-prop-2-ynyl)-carbamic acid tert-butyl ester as a solid. The reaction was stirred at 0° C. for 2 hours, quenched with 10% aqueous potassium carbonate and extracted with ethyl acetate. The combined organics were dried and evaporated. The crude material was purified on 115 g of silica gel, eluting with 80% ethyl acetate/hexanes to afford 4.42 g of E-(3-{4-[3-chloro-4-(6-methyl-pyridin-3-yloxy)-phenylamino]-quinazolin-6-yl}-allyl)-carbamic acid tert-butyl ester. $^1$H NMR (CDCl$_3$): δ 8.66 (s, 1), 8.24 (m, 1), 8.03 (m, 2), 7.77-7.65 (m, 3), 7.13 (m, 2), 6.97 (d, J=8.7 Hz, 1), 6.54 (d, 1), 6.35 (m, 1), 4.9 (m, 1), 3.90 (m, 2), 2.52 (s, 3), 1.46 (s, 9).

E-[6-(3-amino-propenyl)-quinazolin-4-yl]-[3-chloro-4-(6-methyl-pyridin-3-yloxy)-phenyl]-amine. To a solution of 4.42 g of E-(3-{4-[3-chloro-4-(6-methyl-pyridin-3-yloxy) phenylamino]-quinazolin-6-yl}-allyl)-carbamic acid tert-butyl ester in 21 mL of tetrahydrofuran was added 21 mL of 2 N hydrochloric acid. The mixture was heated at 60° C. for 3 hours, cooled to room temperature and basified with 10% aqueous potassium carbonate. Methylene chloride was added to the aqueous mixture and a solid precipitated. The solid was filtered and dried to yield 2.98 g of E-[6-(3-amino-propenyl)-quinazolin-4-yl]-[3-chloro-4-(6-methyl pyridin-3-yloxy)-phenyl]-amine. $^1$H NMR (d$_6$ DMSO): δ 8.62 (s, 1), 8.53 (m, 1), 8.26 (m, 2), 7.99 (m, 1), 7.89 (m, 1), 7.77 (m, 1), 7.30 (m, 3), 6.67 (m, 2), 3.44 (m, 2), 2.47 (s, 3).

E-N-(3-{4-[3-Chloro-4-(6-methyl-pyridin-3-yloxy)-phenylamino]-quinazolin-6-yl}-allyl)-acetamide. A mixture of 14.4 μL (0.25 mmol) of acetic acid and 40.3 mg (0.33 mmol) of dicyclohexylcarbodiimide in 2 mL of methylene chloride were stirred for 10 minutes and treated with 100.3 mg of E-[6-(3-amino-propenyl)-quinazolin-4-yl]-[3-Chloro-4-(6-methyl-pyridin-3-yloxy)-phenyl]-amine. The reaction was allowed to stir at room temperature overnight. The precipitate which formed was filtered and chromatographed on silica gel, eluting with 6-10% methanol/chloroform to afford 106 mg of the title compound; mp 254-256° C.; $^1$H NMR (d$_6$ DMSO): δ 9.88 (s, 1), 8.58 (s, 1), 8.48 (m, 1), 8.20 (m, 3), 7.95 (m, 1), 7.83 (m, 1), 7.71(d, J=8.7 Hz, 1), 7.24 (m, 2), 7.19 (d, J=8.7 Hz, 1), 6.61 (d, J=16.2 Hz, 1), 6.48 (m, 1), 3.90 (m, 2).

Method H: E-2S-Methoxymethyl-pyrrolidine-1-carboxylic acid (3-{4-[3-methyl-4-(6-methyl-pyridin-3-yloxy)-phenylamino]-quinazolin-6-yl}-allyl)-amide (8)

To a stirred solution of 0.125 g (0.31 mmol) of E-[6-(3-amino-propenyl)-quinazolin-4-yl]-[3-methyl-4-(6-methyl-pyridin-3-yloxy)-phenyl]-amine (prepared according to method G) in 1 mL of dichloromethane at 0° C. was added 60.3 μL (0.34 mmol) of Hunig's base followed by dropwise addition of a solution of 48.2 uL (0.34 mmol) of 4-chlorophenyl chloroformate in 1 mL of dichloromethane. The reaction was stirred 30 minutes and evaporated under reduced pressure. The residue was dissolved in 2 mL of dimethyl sulfoxide and 123 μL (0.94 mmol) of (S)-(+)-2-(methoxymethyl)-pyrrolidine was added neat. The mixture was stirred for 3 hours at room temperature. The reaction was quenched into 10% potassium carbonate and extracted with ethyl acetate. The organic layer was washed several times with water and twice with brine. The organic layer was dried over sodium sulfate and reduced to yield the crude material. This material was purified over 90 g of silica gel using 96:4:0.1 chloroform:methanol:ammonium hydroxide as eluent to yield 75 mg (0.14 mmol) of the title compound. $^1$HNMR (d$_6$ DMSO): δ 9.83 (s, 1), 8.56 (s, 2), 8.21 (d, 1), 7.95 (d, 1), 7.80 (d, 1), 7.50 (d, 1), 7.25 (m, 2), 7.01 (d, 1), 6.63 (d, 1), 6.53 (m, 1), 3.95 (m, 2), 3.40 (dd, 1), 3.28 (s, 3), 2.49 (s, 3), 2.24 (s, 3), 1.85 (m, 4).

Method I: E-2-Hydroxy-N-(3-{4-[3-methyl-4-(6-methyl-pyridin-3-yloxy)-phenylamino]-quinazolin-6-yl}-allyl)-isobutyramide (9)

To a solution of 0.170 g (0.42 mmol) of E-[6-(3-amino-propenyl)-quinazolin-4-yl]-[3-methyl-4-(6-methyl-pyridin-3-yloxy)-phenyl]-amine (prepared according to method G) in 1 mL of dichloromethane at 0° C. was added 65 μL (0.47 mmol) of triethylamine followed by a solution of 65 μL (0.45 mmol) of 2-acetoxyisobutyryl chloridein 1 mL of dichloromethane. The reaction was stirred at 0° C. for 1 hour. The mixture was quenched with a dropwise addition of 10% potassium carbonate. The aqueous layer was extracted with dichloromethane and the combined organics were washed with brine, dried over sodium sulfate and evaporated. The crude material was purified on 90 g of silica gel eluting with 96:4:0.1 chloroform/methanol/ammonium hydroxide to afford 2-acetoxy-N-(3-{4-[3-methyl-4-(6-methyl-pyridin-3-yloxy)-phenylamino]-quinazolin-6-yl}-allyl)-isobutyramide. A solution of this material in 2 mL of methanol was treated dropwise with a solution of 41 mg (3.02 mmol) of potassium carbonate in 0.5 mL of water. The solution was stirred at room temperature for 1 hour. The reaction was evaporated and the residue was partitioned between water and chloroform. The aqueous layer was extracted twice with chloroform and the combined organics were washed with brine, dried over sodium sulfate and evaporated to yield 100 mg of the title compound (47%). $^1$HNMR (d$_6$ DMSO): δ 9.78 (s, 1), 8.50 (s, 1), 8.48 (s, 1), 8.15 (d, 1), 7.95 (m, 2), 7.65 (m, 3), 7.21 (m, 2), 6.96 (d, 1), 6.56 (dt, 1), 3.92 (t, 2), 2.46 (s, 3), 2.1.

Method J: Synthesis of Z-Cyclopropanecarboxylic Acid (3-{4-[3-methyl-4-(6-methyl-pyridin-3-yloxy)-phenylamino]quinazolin-6-yl}-allyl)-amide Z-[6-(3-Amino-propenyl)-quinazolin-4-yl]-[3-methyl-4-(6-methyl-pyridin-3-yloxy)-phenyl]-amine: A solution of of (3-{4-[3-Methyl-4-(6-methyl-pyridin-3-yloxy)-phenylamino]-quinazolin-6-yl}-prop-2-ynyl)-carbamic acid tert-butyl ester (1 g, 2.01 mmol) was taken up in methanol (20 ml), palladium in carbon (50 mg) added and the resulting suspension subjected to hydrogenation at 40 psi for eight hours. Thereafter the suspension was filtered through a pad of celite and the filtrate concentrated in vacuo to afford the Z-alkene compound. This was taken up in methanol and HCl (g) was added. Evaporation of solvent then provided Z-[6-(3-Amino-propenyl)-quinazolin-4-yl]-[3-methyl-4-(6-methyl-pyridin-3-yloxy)-phenyl]-amine as its hydrochloride salt. The salt was taken up in CH$_2$Cl$_2$ and stirred with Na$_2$CO$_3$, filtered and solvent evaporated to afford ~700 mg of the free amine.
$^1$H NMR (CD$_3$OD): δ 8.49 (s, 1), 8.31 (s, 1), 8.07 (m, 1), 7.78 (s, 2H), 7.72 (m, 1H), 7.67 (s, 1H), 7.58 (d, J=10.5 Hz, 1H), 7.25 (m, 2H), 6.99 (m 2H), 5.88 (m, 1H), 3.95 (d, J=8 Hz, 2H), 2.47 (s, 3H), 2.23 (s, 3H). MS: M+1, 399.3

Z-Cyclopropanecarboxylic Acid (3-{4-[3-methyl-4-(6-methyl-pyridin-3-yloxy)-phenylamino]-quinazolin-6-yl}-allyl)-amide Z-[6-(3-Amino-propenyl)-quinazolin-4-yl]-[3-methyl-4-(6-methyl-pyridin-3-yloxy)-phenyl]-amine (100 mg, 0.25 mmol) was taken up in DMF (3 ml), HATU (143 mg, 0.38 mmol) and cyclopropane carboxylic acid (36 mg, 0.42 mmol) were added and the resulting solution was allowed to stir for 18 h. Water was then added, the reaction mixture extracted with methylene chloride, the organic extract washed with brine and dried over Na$_2$SO4. After concentration in vacuo, the crude material was subjected to purification on preparative HPLC (reversed phase, 5-40% CH$_3$CN—H$_2$O) to afford 46 mg of the title compound. $^1$H NMR (CD$_3$OD): δ 8.77 (s, 1H), 8.72 (s, 1H), 8.24 (s, 1H), 8.00 (m 1H), 7.77 (m, 3H), 7.55 (m, 2H), 7.07 (d, J=10 Hz, 1H), 6.76 (d, J=113 Hz, 1H), 5.95 (m, 1H), 4.2 (br unresolved m, 2H), 2.59 (s, 3H), 2.3 (s, 3H), 1.59 (br unresolved m, 1H), 1.16 (br unresolved m, 1H), 0.79 (m, 3H). MS: M+1 466.3.

The following examples were prepared using the methods described above.

TABLE I

| Example No. | Name | Method | LRMS | HPLC RT |
|---|---|---|---|---|
| 10 | (±)-[3-Methyl-4-(pyridin-3-yloxy)-phenyl]-(6-piperidin-3-ylethynyl-quinazolin-4-yl)-amine | A | 436.0 | 4.48 |
| 11 | 1-(3-{4-[3-Chloro-4-(6-methyl-pyridin-3-yloxy)-phenylamino]-quinazolin-6-yl}-prop-2-ynyl)-3-cyclopropyl-urea | D | 499.0 | 5.74 |
| 12 | N-(3-{7-Chloro-4-[3-chloro-4-(6-methyl-pyridin-3-yloxy)-phenylamino]-quinazolin-6-yl}-prop-2-ynyl)-acetamide | B | 492.0 | 6.07 |
| 13 | N-(3-{7-Chloro-4-[3-methyl-4-(6-methyl-pyridin-3-yloxy)-phenylamino]-quinazolin-6-yl}-prop-2-ynyl)-acetamide | B | 472.2 | 5.79 |
| 14 | Exo-6-Hydroxymethyl-3-aza-bicyclo[3.1.0]hexane-3-carboxylic acid (3-{4-[3-chloro-4-(6-methyl-pyridin-3-yloxy)-phenylamino]-quinazolin-6-yl}-prop-2-ynyl)-amide | D | 555.0 | 5.19 |
| 15 | 1-(3-{4-[3-Chloro-4-(6-methyl-pyridin-3-yloxy)-phenylamino]-quinazolin-6-yl}-prop-2-ynyl)-3-(2-fluoro-ethyl)-urea | D | 505.0 | 5.65 |
| 16 | 1-(3-{4-[3-Chloro-4-(6-methyl-pyridin-3-yloxy)-phenylamino]-quinazolin-6-yl}-prop-2-ynyl)-3-(2-hydroxy-ethyl)-urea | D | 503.0 | 4.98 |
| 17 | 3-{4-[3-Methyl-4-(pyridin-3-yloxy)-phenylamino]-quinazolin-ylethynyl}-piperidin-3-ol | A | 452.0 | 4.01 |
| 18 | 2-(2-Hydroxy-ethylsulfanyl)-N-(3-{4-[3-methyl-4-(pyridin-3-yloxy)-phenylamino]-quinazolin-6-yl}-prop-2-ynyl)-acetamide | C | 500.0 | 4.87 |
| 19 | N-(3-{4-[3-Chloro-4-(pyridin-3-yloxy)-phenylamino]-quinazolin-6-yl}-prop-2-ynyl)-2-(2-hydroxy-ethylsulfanyl)-acetamide | C | 520.0 | 5.15 |
| 20 | (±)-[3-Methyl-4-(pyridin-3-yloxy)-phenyl]-(6-morpholin-2-ylethynyl-quinazolin-4-yl)-amine | A | 438.0 | 4.29 |

TABLE I-continued

| Example No. | Name | Method | LRMS | HPLC RT |
|---|---|---|---|---|
| 21 | 2-Cyano-N-(3-{4-[3-methyl-4-(pyridin-3-yloxy)-phenylamino]-quinazolin-6-yl}-prop-2-ynyl)-acetamide | B | 448.9 | 5.18 |
| 22 | N-(3-{4-[3-Methyl-4-(pyridin-3-yloxy)-phenylamino]-quinazolin-6-yl}-prop-2-ynyl)-butyramide | B | 452.0 | 5.61 |
| 23 | Pentanoic acid (3-{4-[3-methyl-4-(pyridin-3-Ybloxy)-phenylamino]-quinazolin-6-yl}-prop-2-ynyl)-amide | B | 466.0 | 6.02 |
| 24 | 2-Methoxy-N-(3-{4-[3-methyl-4-(pyridin-3-yloxy)-phenylamino]-quinazolin-6-yl}-prop-2-ynyl)-acetamide | B | 454.0 | 5.24 |
| 25 | N-(4-{4-[3-Methyl-4-(pyridin-3-yloxy)-phenylamino]-quinazolin-6-yl}-but-3-ynyl)-acetamide | B | 438.1 | 5.11 |
| 26 | [6-(4-Amino-but-1-ynyl)-quinazolin-4-yl]-[3-methyl-4-(pyridin-3-yloxy)-phenyl]-amine | A | 396.1 | 4.04 |
| 27 | N-(3-{4-[3-Methyl-4-(pyridin-3-yloxy)-phenylamino]-quinazolin-6-yl}-prop-2-ynyl)-2-methylsulfanyl-acetamide | B | 470.2 | 5.50 |
| 28 | 3-{4-[3-Methyl-4-(pyridin-3-yloxy)-phenylamino]-quinazolin-6-yl}-prop-2-yn-1-ol | B | 383.0 | 4.97 |
| 29 | [6-(3-Methoxy-prop-1-ynyl)-quinazolin-4-yl]-[3-methyl-4-(pyridin-3-yloxy)-phenyl]-amine | B | 397.3 | 6.23 |
| 30 | 4-{4-[3-Methyl-4-(pyridin-3-yloxy)-phenylamino]-quinazolin-6-yl}-but-3-yn-1-ol | B | 397.1 | 5.17 |
| 31 | 2-Methyl-4-{4-[3-methyl-4-(pyridin-3-yloxy)-phenylamino]-quinazolin-6-yl}-but-3-yn-2-ol | B | 411.0 | 5.62 |
| 32 | (3-{4-[3-Methyl-4-(pyridin-3-yloxy)-phenylamino]-quinazolin-6-yl}-prop-2-ynyl)-carbamic acid methyl ester | B | 440.3 | 5.61 |
| 33 | N-(3-{4-[3-Methyl-4-(pyridin-3-yloxy)-phenylamino]-quinazolin-6-yl}-prop-2-ynyl)-methanesulfonamide | B | 460.0 | 5.38 |
| 34 | N-(3-{4-[3-Methyl-4-(pyridin-3-yloxy)-phenylamino]-quinazolin-6-yl}-prop-2-ynyl)-acetamide | B | 424.1 | 4.94 |
| 35 | [3-Methoxy-4-(pyridin-3-yloxy)-pheny]-(6-piperidin-3-ylethynyl-quinazolin-4-yl)-amine | A | 452.0 | 4.10 |
| 36 | 2-Chloro-N-(3-{4-[3-methyl-4-(pyridin-3-yloxy)-phenylamino]-quinazolin-6-yl}-prop-2-ynyl)-acetamide | B | 458.0 | 5.52 |
| 37 | 2-Methylamino-N-(3-{4-[3-methyl-4-(pyridin-3-yloxy)-phenylamino]-quinazolin-6-yl}-prop-2-ynyl)-acetamide | C | 453.1 | 4.08 |
| 38 | 2-Dimethylamino-N-(3-{4-[3-methyl-4-(pyridin-3-yloxy)-phenylamino]-quinazolin-6-yl}-prop-2-ynyl)-acetamide | C | 467.3 | 4.15 |
| 39 | (±)-(6-Piperidin-3-ylethynyl-quinazolin-4-yl)-[4-(pyridin-3-yloxy)-phenyl]-amine | A | 422.1 | 4.13 |
| 40 | [3-Methoxy-4-(pyridin-3-yloxy)-phenyl]-(6-piperidin-4-quinazolin-4-yl)-amine | A | 452.1 | 4.11 |
| 41 | [3-Chloro-4-(pyridin-3-yloxy)-phenyl]-(6-piperidin-4-ylethynyl-quinazolin-4-yl)-amine | A | 456.1 | 4.57 |
| 42 | [3-Fluoro-4-(pyridin-3-yloxy)-phenyl]-(6-piperidin-4-ylethynyl-quinazolin-4-yl)-amine | A | 440.1 | 4.38 |
| 43 | (6-Piperidin-4-ylethynyl-quinazolin-4-yl)-[4-(pyridin-3-yloxy)-phenyl]-amine | A | 422.1 | 4.11 |
| 44 | 2-Methoxy-N-(3-{4-[3-methoxy-4-(pyridin-3-yloxy)-phenylamino]-quinazolin-6-yl}-prop-2-ynyl)-acetamide | B | 470.3 | 4.87 |
| 45 | N-(3-{4-[3-Chloro-4-(pyridin-3-yloxy)-phenylamino]-quinazolin-6-yl}-prop-2-ynyl)-2-methoxy-acetamide | B | 474.2 | 5.48 |
| 46 | N-(3-{4-[3-Fluoro-4-(pyridin-3-yloxy)-phenylamino]-quinazolin-6-yl}-prop-2-ynyl)-2-methoxy-acetamide | B | 458.3 | 5.23 |

TABLE I-continued

| Example No. | Name | Method | LRMS | HPLC RT |
|---|---|---|---|---|
| 47 | [3-Methyl-4-(pyridin-2-yloxy)-phenyl]-(6-piperidin-4-ylethynyl-quinazolin-4-yl)-amine | A | 436.0 | 4.52 |
| 48 | 2,2-Dimethyl-N-(3-{4-[3-methyl-4-(pyridin-3-yloxy)-phenylamino]-quinazolin-6-yl}-prop-2-ynyl)-propionamide | A | 452.3 | 5.60 |
| 49 | N-(3-{4-[3-Methyl-4-(pyridin-3-yloxy)-phenylamino]-quinazolin-6-yl}-prop-2-ynyl)-isobutyramide | B | 466.3 | 6.01 |
| 50 | {6-[3-(2-Methoxy-ethoxy)-prop-1-ynyl]-quinazolin-4-yl}-[3-methyl-4-(pyridin-3-yloxy)-phenyl]-amine | B | 441.1 | 6.11 |
| 51 | 2-Diethylamino-N-(3-{4-[3-methyl-4-(pyridin-3-yloxy)-phenylamino]-quinazolin-6-yl}-prop-2-ynyl)-acetamide | C | 495.1 | 4.45 |
| 52 | (±)-[3-Methyl-4-(2-methyl-pyridin-3-yloxy)-phenyl]-(6-piperidin-3-ylethynyl-quinazolin-4-yl)-amine | A | 450.0 | 4.47 |
| 53 | [3-Methyl-4-(2-methyl-pyridin-3-yloxy)-phenyl]-(6-piperidin-4-ylethynyl-quinazolin-4-yl)-amine | A | 450.0 | 4.39 |
| 54 | 2-Methoxy-N-(3-{4-[3-methyl-4-(2-methyl-pyridin-3-yloxy)-phenylamino]-quinazolin-6-yl}-prop-2-ynyl)-acetamide | B | 468.0 | 5.33 |
| 55 | 2-(2-Methoxy-ethoxy)-N-(3-{4-[3-methyl-4-(pyridin-3-yloxy)-phenylamino]-quinazolin-6-yl}-prop-2-ynyl)-acetamide | B | 498.3 | 5.34 |
| 56 | (±)-Tetrahydro-furan-2-carboxylic acid (3-{4-[3-methyl-4-(pyridin-3-yloxy)-phenylamino]-quinazolin-6-yl}-prop-2-ynyl)-amide | B | 480.0 | 5.45 |
| 57 | (±)-4,4-Dimethyl-5-{4-[3-methyl-4-(pyridin-3-yloxy)-phenylamino]-quinazolin-6-ylethynyl}-oxazolidin-2-one | B | 466.0 | 5.70 |
| 58 | {6-[4-(2-Methoxy-ethoxy)-but-1-ynyl]-quinazolin-4-yl}-[3-methyl-4-(pyridin-3-yloxy)-phenyl]-amine | B | 455.3 | 6.23 |
| 59 | 4-{4-[3-Methyl-4-(pyridin-3-yloxy)-phenylamino]-quinazolin-6-ylethynyl}-piperidin-4-ol | A | 452.0 | 3.82 |
| 60 | 1-Methyl-4-{4-[3-methyl-4-(pyridin-3-yloxy)-phenylamino]-quinazolin-6-ylethynyl}-piperidin-4-ol | B | 466.1 | 4.03 |
| 61 | (±)-[3-Methyl-4-(6-methyl-pyridin-3-yloxy)-phenyl]-(6-piperidin-3-ylethynyl-quinazolin-4-yl)-amine | A | 450.0 | 4.52 |
| 62 | [3-Methyl-4-(6-methyl-pyridin-3-yloxy)-phenyl]-(6-piperidin-4-ylethynyl-quinazolin-4-yl)-amine | A | 450.0 | 4.49 |
| 63 | 2-Methoxy-N-(3-{4-[3-methyl-4-(6-methyl-pyridin-3-yloxy)-phenylamino]-quinazolin-6-yl}-prop-2-ynyl)-acetamide | B | 468.8 | 5.38 |
| 64 | [6-(4-Methoxy-but-1-ynyl)-quinazolin-4-yl]-[3-methyl-4-(pyridin-3-yloxy)-phenyl]-amine | B | 411.2 | 6.30 |
| 65 | (±)-[4-(2-Chloro-pyridin-3-yloxy)-3-methyl-phenyl]-(6-piperidin-3-ylethynyl-quinazolin-4-yl)-amine | A | 470.0 | 4.89 |
| 66 | Cyclopropanecarboxylic acid (4-{4-[3-methyl-4-(pyridin-3-yloxy)-phenylamino]-quinazolin-6-yl}-but-3-ynyl)-amide | B | 464.3 | 5.63 |
| 67 | [4-(2-Chloro-pyridin-3-yloxy)-3-methyl-phenyl]-(6-piperidin-4-ylethynyl-quinazolin-4-yl)-amine | A | 470.0 | 4.86 |
| 68 | N-(3-{4-[4-(2-Chloro-pyridin-3-yloxy)-3-methyl-phenylamino]-quinazolin-6-yl}-prop-2-ynyl)-2-methoxy-acetamide | B | 488.0 | 5.84 |
| 69 | N-(4-{4-[3-Methyl-4-(pyridin-3-yloxy)-phenylamino]-quinazolin-6-yl}-but-3-ynyl)-2-methylsulfanyl-acetamide | B | 484.2 | 5.64 |
| 70 | [3-Chloro-4-(pyridin-3-yloxy)-phenyl]-[6-(4-methoxy-but-1-ynyl)-quinazolin-4-yl]-amine | B | 431.1 | 6.67 |
| 71 | (±)-4-{4-[3-Methyl-4-(pyridin-3-yloxy)-phenylamino]-quinazolin-6-yl}-but-3-yne-1,2-diol | A | 413.1 | 4.31 |

TABLE I-continued

| Example No. | Name | Method | LRMS | HPLC RT |
|---|---|---|---|---|
| 72 | (±)-[3-Methyl-4-(pyridin-4-yloxy)-phenyl]-(6-piperidin-3-ylethynyl-quinazolin-4-yl)-amine | A | 434.1 | 3.88 |
| 73 | [3-Methyl-4-(pyridin-4-yloxy)-phenyl]-(6-piperidin-4-ylethynyl-quinazolin-4-yl)-amine | A | 436.1 | 3.91 |
| 74 | 2-Methoxy-N-(3-{4-[3-methyl-4-(pyridin-4-yloxy)-phenylamino]-quinazolin-6-yl}-prop-2-ynyl)-acetamide | B | 452.0 | 4.71 |
| 75 | 2,2-Difluoro-N-(3-{4-[3-methyl-4-(pyridin-3-yloxy)-phenylamino]-quinazolin-6-yl}-prop-2-ynyl)-acetamide | B | 460.2 | 5.63 |
| 76 | N-(3-{4-[3-Chloro-4-(pyridin-3-yloxy)-phenylamino]-quinazolin-6-yl}-prop-2-ynyl)-2,2-difluoro-acetamide | B | 482.2, 480.1 | 5.92 |
| 77 | R-Pyrrolidine-2-carboxylic acid (3-{4-[3-methyl-4-(pyridin-3-yloxy)-phenylamino]-quinazolin-6-yl}-prop-2-ynyl)-amide | A | 479.1 | 4.22 |
| 78 | (±)-Tetrahydro-furan-3-carboxylic acid (3-{4-[3-chloro-4-(pyridin-3-yloxy)-phenylamino]-quinazolin-6-yl}-prop-2-ynyl)-amide | B | 500.0 | 5.39 |
| 79 | Cyclopropanecarboxylic acid (4-{4-[3-chloro-4-(pyridin-3-yloxy)-phenylamino]-quinazolin-6-yl}-but-3-ynyl)-amide | B | 484.0 | 5.92 |
| 80 | N-(4-{4-[3-Chloro-4-(pyridin-3-yloxy)-phenylamino]-quinazolin-6-yl}-but-3-ynyl)-2-methylsulfanyl-acetamide | B | 505.4 | 5.91 |
| 81 | 1-(3-{4-[3-Methyl-4-(pyridin-3-yloxy)-phenylamino]-quinazolin-6-yl}-prop-2-ynyl)-3-phenyl-urea | D | 501.1 | 6.17 |
| 82 | 1-Cyclohexyl-3-(3-{4-[3-methyl-4-(pyridin-3-yloxy)-phenylamino]-quinazolin-6-yl}-prop-2-ynyl)-urea | D | 507.2 | 6.24 |
| 83 | 1-(3-{4-[3-Chloro-4-(pyridin-3-yloxy)-phenylamino]-quinazolin-6-yl}-prop-2-ynyl)-3-cyclohexyl-urea | D | 528.1 | 6.49 |
| 84 | 2-Hydroxy-N-(4-{4-[3-methyl-4-(pyridin-3-yloxy)-phenylamino]-quinazolin-6-yl}-but-3-ynyl)-acetamide | A | 454.2 | 4.78 |
| 85 | E-3-{4-[3-Methyl-4-(pyridin-3-yloxy)-phenylamino]-quinazolin-6-yl}-prop-2-en-1-ol | E | 385.1 | 4.71 |
| 86 | E-[3-Methyl-4-(pyridin-3-yloxy)-phenyl]-[6-(3-morpholin-4-yl-propenyl)-quinazolin-4-yl]-amine | F | 454.1 | 4.14 |
| 87 | 2-Methanesulfonyl-N-(3-{4-[3-methyl-4-(pyridin-3-yloxy)-phenylamino]-quinazolin-6-yl}-prop-2-ynyl)-acetamide | B | 502.0 | 5.00 |
| 88 | N-(3-{4-[3-Chloro-4-(pyridin-3-yloxy)-phenylamino]-quinazolin-6-yl}-prop-2-ynyl)-2-methanesulfonyl-acetamide | B | 522.0 | 5.28 |
| 89 | (3-{4-[3-Methyl-4-(pyridin-3-yloxy)-phenylamino]-quinazolin-6-yl}-prop-2-ynyl)-thiocarbamic acid S-methyl ester | B | 456.2 | 6.02 |
| 90 | (3-{4-[3-Chloro-4-(pyridin-3-yloxy)-phenylamino]-quinazolin-6-yl}-prop-2-ynyl)-thiocarbamic acid S-methyl ester | B | 476.1 | 6.29 |
| 91 | [4-(2-Methyl-pyridin-3-yloxy)-phenyl]-(6-piperidin-4-ylethynyl-quinazolin-4-yl)-amine | A | 436.1 | 4.24 |
| 92 | (±)-[4-(2-Methyl-pyridin-3-yloxy)-phenyl]-(6-piperidin-3-ylethynyl-quinazolin-4-yl)-amine | A | 436.0 | 4.85 |
| 93 | N-(3-{4-[4-(2-Methyl-pyridin-3-yloxy)-phenylamino]-quinazolin-6-yl}-prop-2-ynyl)-acetamide | B | 424.1 | 4.85 |
| 94 | N-(3-{4-[3-Methyl-4-(pyridin-3-yloxy)-phenylamino]-quinazolin-yl}-prop-2-ynyl)-2-oxo-propionamide | B | 452.1 | 5.64 |
| 95 | N-(3-{4-[3-Chloro-4-(pyridin-3-yloxy)-phenylamino]-quinazolin-6-yl}-prop-2-ynyl)-2-oxo-propionamide | B | 474.3, 472.3 | 5.93 |
| 96 | N-(3-{4-[3-Methyl-4-(pyridin-3-yloxy)-phenylamino]-quinazolin-6-yl}-prop-2-ynyl)-malonamic acid ethyl ester | B | 496.2 | 5.56 |

TABLE I-continued

| Example No. | Name | Method | LRMS | HPLC RT |
|---|---|---|---|---|
| 97 | N-(3-{4-[3-Chloro-4-(pyridin-3-yloxy)-phenylamino]-quinazolin-6yl}-prop-2-ynyl)-malonamic acid ethyl ester | B | 516.0 | 5.84 |
| 98 | N-(1,1-Dimethyl-3-{4-[3-methyl-4-(pyridin-3-yloxy)-phenylamino]-quinazolin-6-yl}-prop-2-ynyl)-2,2,2-trifluoro-acetamide | B | 506.0 | 6.76 |
| 99 | (±)-N-(1-Hydroxymethyl-3-{4-[3-methyl-4-(pyridin-3-yloxy)-phenylamino]-quinazolin-6-yl}-prop-2-ynyl)-acetamide | B | 454.1 | 4.47 |
| 100 | (±)-[3-Ethynyl-4-(pyridin-3-yloxy)-phenyl]-(6-piperidin-3-ylethynyl-quinazolin-4-yl)-amine | A | 446.1 | 4.33 |
| 101 | [3-Ethynyl-4-(pyridin-3-yloxy)-phenyl]-(6-piperidin-4-ylethynyl-quinazolin-4-yl)-amine | A | 446.1 | 4.27 |
| 102 | 3-{4-[3-Chloro-4-(pyridin-3-yloxy)-phenylamino]-quinazolin-6-yl}-prop-2-yn-1-ol | B | 403.1 | 5.43 |
| 103 | (±)-N-(1-Hydroxymethyl-3-{4-[3-methyl-4-(6-methyl-pyridin-3-yloxy)-phenylamino]-quinazolin-6-yl}-prop-2-ynyl)-acetamide | B | 468.1 | 4.66 |
| 104 | (±)-N-(3-{4-[3-Chloro-4-(pyridin-3-yloxy)-phenylamino]-quinazolin-6-yl}-1-hydroxymethyl-prop-2-ynyl)-acetamide | b | 474.0 | 4.78 |
| 105 | 2,2-Difluoro-N-(3-{4-[3-methyl-4-(6-methyl-pyridin-3-yloxy)-phenylamino]-quinazolin-6-yl}-prop-2-ynyl)-acetamide | B | 474.2 | 5.83 |
| 106 | 2-Methanesulfonyl-N-(3-{4-[3-methyl-4-(6-methyl-pyridin-3-yloxy)-phenylamino]-quinazolin-6-yl}-prop-2-ynyl)-acetamide | B | 516.0 | 5.20 |
| 107 | 2-Fluoro-N-(3-{4-[3-methyl-4-(pyridin-3-yloxy)-phenylamino]-quinazolin-6-yl}-prop-2-ynyl)-acetamide | B | 441.8 | 5.27 |
| 108 | N-(3-{4-[3-Chloro-4-(pyridin-3-yloxy)-phenylamino]-quinazolin-6-yl}-prop-2-ynyl)-2-fluoro-acetamide | B | 461.9 | 5.55 |
| 109 | 2-Fluoro-N-(3-{4-[3-methyl-4-(6-methyl-pyridin-3-yloxy)-phenylamino]-quinazolin-6-yl}-prop-2-ynyl)-acetamide | B | 456.2 | 5.47 |
| 110 | N-(3-{4-[3-Ethynyl-4-(pyridin-3-yloxy)-phenylamino]-quinazolin-6-yl}-prop-2-ynyl)-2-methoxy-acetamide | B | 464.1 | 5.16 |
| 111 | 2-Methoxy-N-(3-{4-[4-(2-methyl-pyridin-3-yloxy)-phenylamino]-quinazolin-6-yl}-prop-2-ynyl)-acetamide | B | 454.2 | 5.15 |
| 112 | [4-(2-Chloro-pyridin-3-yloxy)-phenyl]-(6-piperidin-4-ylethynyl-quinazolin-4-yl)-amine | A | 456.1 | 4.64 |
| 113 | (±)-[4-(2-Chloro-pyridin-3-yloxy)-phenyl]-(6-piperidin-3-ylethynyl-quinazolin-4-yl)-amine | A | 456.0 | 4.67 |
| 114 | N-(3-{4-[4-(2-Chloro-pyridin-3-yloxy)-phenylamino]-quinazolin-6-yl}-prop-2-ynyl)-2-methoxy-acetamide | B | 474.0 | 5.54 |
| 115 | N-(3-{4-[4-(2-Chloro-pyridin-3-yloxy)-phenylamino]-quinazolin-6-yl}-prop-2-ynyl)-acetamide | B | 444.0 | 5.25 |
| 116 | N-(3-{4-[3-Ethynyl-4-(pyridin-3-yloxy)-phenylamino]-quinazolin-6-yl}-prop-2-ynyl)-acetamide | B | 434.1 | 4.88 |
| 117 | 1-(2-Chloro-ethyl)-3-(3-{4-[3-methyl-4-(pyridin-3-yloxy)-phenylamino]-quinazolin-6-yl}-prop-2-ynyl)-urea | D | 487.2 | 5.46 |
| 118 | (±)-[3-Fluoro-4-(2-methyl-pyridin-3-yloxy)-phenyl]-(6-piperidin-3-ylethynyl-quinazolin-4-yl)-amine | A | 454.1 | 4.57 |
| 119 | [3-Fluoro-4-(2-methyl-pyridin-3-yloxy)-phenyl]-(6-piperidin-4-ylethynyl-quinazolin-4-yl)-amine | A | 454.1 | 4.56 |
| 120 | N-(3-{4-[3-Fluoro-4-(2-methyl-pyridin-3-yloxy)-phenylamino]-quinazolin-6-yl}-prop-2-ynyl)-acetamide | B | 442.1 | 5.19 |
| 121 | N-(3-{4-[3-Chloro-4-(6-methyl-pyridin-3-yloxy)-phenylamino]-quinazolin-6-yl}-prop-2-ynyl)-acetamide | B | 458.0 | 5.48 |

TABLE I-continued

| Example No. | Name | Method | LRMS | HPLC RT |
|---|---|---|---|---|
| 122 | [3-Chloro-4-(6-methyl-pyridin-3-yloxy)-phenyl]-(6-piperidin-4-ylethynyl-quinazolin-4-yl)-amine | A | 470.0 | 4.78 |
| 123 | (±)-[3-Chloro-4-(6-methyl-pyridin-3-yloxy)-phenyl]-(6-piperidin-3-ylethynyl-quinazolin-4-yl)-amine | A | 470.0 | 4.80 |
| 124 | Acetic acid 3-{4-[3-methyl-4-(pyridin-3-yloxy)-phenylamino]-quinazolin-6-yl}-prop-2-ynyl ester | B | 425.1 | 6.34 |
| 125 | 3-{4-[3-Methyl-4-(6-methyl-pyridin-3-yloxy)-phenylamino]-quinazolin-6-yl}-prop-2-yn-1-ol | B | 397.2 | 5.31 |
| 126 | Acetic acid 3-{4-[3-methyl-4-(6-methyl-pyridin-3-yloxy)-phenylamino]-quinazolin-6-yl}-prop-2-ynyl ester | B | 439.1 | 6.57 |
| 127 | Acetic acid 3-{4-[3-chloro-4-(pyridin-3-yloxy)-phenylamino]-quinazolin-6-yl}-prop-2-ynyl ester | B | 445.1 | 6.66 |
| 128 | 2-Hydroxy-N-(3-{4-[3-methyl-4-(6-methyl-pyridin-3-yloxy)-phenylamino]-quinazolin-6-yl}-prop-2-ynyl)-acetamide | A | 454.2 | 4.81 |
| 129 | N-(3-{4-[3-Methyl-4-(6-methyl-pyridin-3-yloxy)-phenylamino]-quinazolin-6-yl}-prop-2-ynyl)-acetamide | B | 438.0 | 5.20 |
| 130 | R-Pyrrolidine-2-carboxylic acid (3-{4-[3-methyl-4-(6-methyl-pyridin-3-yloxy)-phenylamino]-quinazolin-6-yl}-prop-2-ynyl)-amide | A | 493.0 | 4.42 |
| 131 | 2-(2-Hydroxy-ethylsulfanyl)-N-(3-{4-[3-methyl-4-(6-methyl-pyridin-3-yloxy)-phenylamino]-quinazolin-6-yl}-prop-2-ynyl)-acetamide | C | 513.9 | 5.07 |
| 132 | (±)-2-Methanesulfinyl-N-(3-{4-[3-methyl-4-(6-methyl-pyridin-3-yloxy)-phenylamino]-quinazolin-6-yl}-prop-2-ynyl)-acetamide | B | 499.9 | 4.71 |
| 133 | (3-{4-[3-Methyl-4-(6-methyl-pyridin-3-yloxy)-phenylamino]-quinazolin-6-yl}-prop-2-ynyl)-thiocarbamic acid S-methyl ester | B | 469.9 | 6.25 |
| 134 | (±)-Tetrahydro-furan-3-carboxylic acid (3-{4-[3-methyl-4-(6-methyl-pyridin-3-yloxy)-phenylamino]-quinazolin-6-yl}-prop-2-ynyl)-amide | B | 494.0 | 5.31 |
| 135 | N-(3-{4-[3-Methyl-4-(6-methyl-pyridin-3-yloxy)-phenylamino]-quinazolin-6-yl}-prop-2-ynyl)-2-oxo-propionamide | B | 465.9 | 5.87 |
| 136 | N-(3-{4-[3-Methyl-4-(6-methyl-pyridin-3-yloxy)-phenylamino]-quinazolin-6-yl}-prop-2-ynyl)-malonamic acid ethyl ester | B | 510.0 | 5.77 |
| 137 | (6-Piperidin-4-ylethynyl-quinazolin-4-yl)-[4-(pyridin-2-yloxy)-phenyl]-amine | A | 422.2 | 3.48 |
| 138 | (±)-(6-Piperidin-3-ylethynyl-quinazolin-4-yl)-[4-(pyridin-2-yloxy)-phenyl]-amine | A | 422.2 | 3.51 |
| 139 | N-(3-{4-[4-(Pyridin-2-yloxy)-phenylamino]-quinazolin-6-yl}-prop-2-ynyl)-acetamide | B | 410.1 | 3.81 |
| 140 | 2-Methylamino-N-(3-{4-[3-methyl-4-(6-methyl-pyridin-3-yloxy)-phenylamino]-quinazolin-6-yl}-prop-2-ynyl)-acetamide | C | 467.0 | 4.26 |
| 141 | 2-Dimethylamino-N-(3-{4-[3-methyl-4-(6-methyl-pyridin-3-yloxy)-phenylamino]-quinazolin-6-yl}-prop-2-ynyl)-acetamide | C | 481.0 | 4.26 |
| 142 | (±)-N-(3-{4-[3-Chloro-4-(6-methyl-pyridin-3-yloxy)-phenylamino]-quinazolin-6-yl}-1-hydroxymethyl-prop-2-ynyl)-acetamide | B | 488.0 | 4.99 |
| 143 | N-(3-{4-[3-Chloro-4-(6-methyl-pyridin-3-yloxy)-phenylamino]-quinazolin-6-yl}-prop-2-ynyl)-2-dimethylamino-acetamide | C | 501.0 | 4.83 |
| 144 | N-(3-{4-[3-Chloro-4-(6-methyl-pyridin-3-yloxy)-phenylamino]-quinazolin-6-yl}-prop-2-ynyl)-2-methoxy-acetamide | B | 488.0 | 5.79 |
| 145 | N-(3-{4-[3-Chloro-4-(6-methyl-pyridin-3-yloxy)-phenylamino]-quinazolin-6-yl}-prop-2-ynyl)-2-fluoro-acetamide | B | 476.0 | 5.79 |
| 146 | N-(3-{4-[3-Chloro-4-(6-methyl-pyridin-3-yloxy)-phenylamino]-quinazolin-6-yl}-prop-2-ynyl)-2,2-difluoro-acetamide | B | 494.0 | 6.14 |

TABLE I-continued

| Example No. | Name | Method | LRMS | HPLC RT |
|---|---|---|---|---|
| 147 | E-3-{4-[3-Chloro-4-(pyridin-3-yloxy)-phenylamino]-quinazolin-6-yl}-prop-2-en-1-ol | E | 405.1 | 5.04 |
| 148 | 2-Methoxy-N-(3-{4-[4-(pyridin-2-yloxy)-phenylamino]-quinazolin-6-yl}-prop-2-ynyl)-acetamide | B | 440.8 | 4.05 |
| 149 | 1-Ethyl-3-(3-{4-[3-methyl-4-(6-methyl-pyridin-3-yloxy)-phenylamino]-quinazolin-6-yl}-prop-2-ynyl)-urea | D | 467.2 | 5.36 |
| 150 | 1-(3-{4-[3-Chloro-4-(pyridin-3-yloxy)-phenylamino]-quinazolin-6-yl}-prop-2-ynyl)-3-ethyl-urea | D | 473.2 | 5.45 |
| 151 | 1-Ethyl-3-(3-{4-[3-methyl-4-(pyridin-3-yloxy)-phenylamino]-quinazolin-6-yl}-prop-2-ynyl)-urea | D | 453.1 | 5.16 |
| 152 | 1-(3-{4-[3-Chloro-4-(6-methyl-pyridin-3-yloxy)-phenylamino]-quinazolin-6-yl}-prop-2-ynyl)-3-ethyl-urea | D | 487.1 | 5.60 |
| 153 | (±)-2-Hydroxy-N-(3-{4-[3-methyl-4-(pyridin-3-yloxy)-phenylamino]-quinazolin-6-yl}-prop-2-ynyl)-propionamide | A | 454.1 | 4.79 |
| 154 | N-(3-{4-[3-Methyl-4-(2-methyl-pyridin-3-yloxy)-phenylamino]-quinazolin-6-yl}-prop-2-ynyl)-2-oxo-propionamide | B | 466.1 | 5.85 |
| 155 | N-(3-{4-[3-Methyl-4-(2-methyl-pyridin-3-yloxy)-phenylamino]-quinazolin-6-yl}-prop-2-ynyl)-acetamide | B | 438.1 | 5.18 |
| 156 | (±)-2-Hydroxy-N-(3-{4-[3-methyl-4-(6-methyl-pyridin-3-yloxy)-phenylamino]-quinazolin-6-yl}-prop-2-ynyl)-propionamide | A | 468.0 | 4.98 |
| 157 | (±)-N-(3-{4-[3-Chloro-4-(6-methyl-pyridin-3-yloxy)-phenylamino]-quinazolin-6-yl}-prop-2-ynyl)-2-hydroxy-propionamide | A | 488.0 | 5.32 |
| 158 | N-(3-{4-[3-Methyl-4-(6-methyl-pyridin-3-yloxy)-phenylamino]-quinazolin-6-yl}-prop-2-ynyl)-2-(4-methyl-piperazin-1-yl)-acetamide | C | 536.2 | 4.46 |
| 159 | 2-[Bis-(2-methoxy-ethyl)-amino]-N-(3-{4-[3-methyl-4-(6-methyl-pyridin-3-yloxy)-phenylamino]-quinazolin-6-yl}-prop-2-ynyl)-acetamide | C | 569.1 | 5.93 |
| 160 | 2-(2-Hydroxy-ethylamino)-N-(3-{4-[3-methyl-4-(pyridin-3-yloxy)-phenylamino]-quinazolin-6-yl}-prop-2-ynyl)-acetamide | C | 483.0 | 4.11 |
| 161 | N-(3-{4-[3-Chloro-4-(pyridin-3-yloxy)-phenylamino]-quinazolin-6-yl}-prop-2-ynyl)-2-dimethylamino-acetamide | C | 487.0 | 4.65 |
| 162 | N-(3-{4-[3-Chloro-4-(pyridin-3-yloxy)-phenylamino]-quinazolin-6-yl}-prop-2-ynyl)-2-methylamino-acetamide | C | 473.0 | 4.42 |
| 163 | N-(3-{4-[3-Chloro-4-(6-methyl-pyridin-3-yloxy)-phenylamino]-quinazolin-6-yl}-prop-2-ynyl)-2-methylamino-acetamide | C | 487.1 | 4.60 |
| 164 | N-(3-{4-[3-Chloro-4-(6-methyl-pyridin-3-yloxy)-phenylamino]-quinazolin-6-yl}-prop-2-ynyl)-2-hydroxy-acetamide | A | 474.0 | 5.13 |
| 165 | 1-(3-{4-[3-Chloro-4-(6-methyl-pyridin-3-yloxy)-phenylamino]-quinazolin-6-yl}-prop-2-ynyl)-3-isopropyl-urea | D | 501.8 | 5.98 |
| 166 | 1-Isopropyl-3-(3-{4-[3-methyl-4-(6-methyl-pyridin-3-yloxy)-phenylamino]-quinazolin-6-yl}-prop-2-ynyl)-urea | D | 481.0 | 5.69 |
| 167 | Morpholine-4-carboxylic acid (3-{4-[3-methyl-4-(6-methyl-pyridin-3-yloxy)-phenylamino]-quinazolin-6-yl}-prop-2-ynyl)-amide | D | 509.1 | 5.27 |
| 168 | N-(3-{4-[3-Chloro-4-(6-methyl-pyridin-3 yloxy)-phenylamino]-quinazolin-6-yl}-prop-2-ynyl)-2-morpholin-4-yl-acetamide | C | 543.3 | 5.64 |
| 169 | N-(3-{4-[3-Methyl-4-(6-methyl-pyridin-3-yloxy)-phenylamino]-quinazolin-6-yl}-prop-2-ynyl)-2-morpholin-4-yl-acetamide | C | 522.8 | 5.37 |
| 170 | [6-(3-Amino-prop-1-ynyl)-quinazolin-4-yl]-[3-methyl-4-(6-methyl-pyridin-3-yloxy)-phenyl]-amine | A | 396.3 | 4.05 |

TABLE I-continued

| Example No. | Name | Method | LRMS | HPLC RT |
|---|---|---|---|---|
| 171 | E-[6-(3-Amino-propenyl)-quinazolin-4-yl]-[3-methyl-4-(6-methyl-pyridin-3-yloxy)-phenyl]-amine | G | 398.2 | 3.87 |
| 172 | E-[6-(3-Amino-propenyl)-quinazolin-4-yl]-[3-chloro-4-(6-methyl-pyridin-3-yloxy)-phenyl]-amine | G | 418.0 | 4.26 |
| 173 | 2-Hydroxy-N-(3-{4-[3-methyl-4-(pyridin-3-yloxy)-phenylamino]-quinazolin-6-yl}-prop-2-ynyl)-isobutyramide | A | 468.1 | 5.04 |
| 174 | 2-Hydroxy-N-(3-{4-[3-methyl-4-(6-methyl-pyridin-3-yloxy)-phenylamino]-quinazolin-6-yl}-prop-2-ynyl)-isobutyramide | A | 482.1 | 5.24 |
| 175 | N-(3-{4-[3-Chloro-4-(6-methyl-pyridin-3-yloxy)-phenylamino]-quinazolin-6-yl}-prop-2-ynyl)-2-hydroxy-isobutyramide | A | 502.0, 504.0 | 5.55 |
| 176 | [6-(3-Amino-prop-1-ynyl)-quinazolin-4-yl]-[3-chloro-4-(6-methyl-pyridin-3-yloxy)-phenyl]-amine | A | 416.2 | 4.25 |
| 177 | N-(3-{4-[3-Methyl-4-(6-methyl-pyridin-3-yloxy)-phenylamino]-quinazolin-6-yl}-prop-2-ynyl)-2-(2,2,2-trifluoro-ethylamino)-acetamide | C | 535.3 | 5.99 |
| 178 | 1,1-Dimethyl-3-(3-{4-[3-methyl-4-(6-methyl-pyridin-3-yloxy)-phenylamino]-quinazolin-6-yl}-prop-2-ynyl)-urea | D | 467.3 | 5.36 |
| 179 | 3-(3-{4-[3-Chloro-4-(6-methyl-pyridin-3-yloxy)-phenylamino]-quinazolin-6-yl}-prop-2-ynyl)-1,1-diethyl-urea | D | 515.0 | 6.32 |
| 180 | 3-(3-{4-[3-Chloro-4-(6-methyl-pyridin-3-yloxy)-phenylamino]-quinazolin-6-yl}-prop-2-ynyl)-1,1-dimethyl-urea | D | 487.1 | 5.70 |
| 181 | E-N-(3-{4-[3-Methyl-4-(6-methyl-pyridin-3-yloxy)-phenylamino]-quinazolin-6-yl}-allyl)-acetamide | G | 440.3 | 4.74 |
| 182 | E-2-Methoxy-N-(3-{4-[3-methyl-4-(6-methyl-pyridin-3-yloxy)-phenylamino]-quinazolin-6-yl}-allyl)-acetamide | G | 470.1 | 5.05 |
| 183 | Morpholine-4-carboxylic acid (3-{4-[3-chloro-4-(6-methyl-pyridin-3-yloxy)-phenylamino]-quinazolin-6-yl}-prop-2-ynyl)-amide | D | 529.0 | 5.58 |
| 184 | Pyrrolidine-1-carboxylic acid (3-{4-[3-chloro-4-(6-methyl-pyridin-3-yloxy)-phenylamino]-quinazolin-6-yl}-prop-2-ynyl)-amide | D | 513.0 | 6.00 |
| 185 | 1-(3-{4-[3-Chloro-4-(6-methyl-pyridin-3-yloxy)-phenylamino]-quinazolin-6-yl}-prop-2-ynyl)-3-methyl-urea | D | 473.0 | 5.37 |
| 186 | 1-(3-{4-[3-Chloro-4-(6-methyl-pyridin-3-yloxy)-phenylamino]-quinazolin-6-yl}-prop-2-ynyl)-3-propyl-urea | D | 501.0 | 6.03 |
| 187 | 1-tert-Butyl-3-{3-{4-[3-chloro-4-(6-methyl-pyridin-3-yloxy)-phenylamino]-quinazolin-6-yl}-prop-2-ynyl)-urea | D | 515.0 | 6.56 |
| 188 | 2S-Hydroxy-N-(3-{4-[3-methyl-4-(6-methyl-pyridin-3-yloxy)-phenylamino]-quinazolin-6-yl}-prop-2-ynyl)-propionamide | B | 468.0 | 4.95 |
| 189 | 1-(3-{4-[3-Chloro-4-(6-methyl-pyridin-3-yloxy)-phenylamino]-quinazolin-6-yl}-prop-2-ynyl)-3-(2,2,2-trifluoro-ethyl)-urea | D | 540.7 | 6.19 |
| 190 | (±)-Azetidine-2-carboxylic acid (3-{4-[3-methyl-4-(pyridin-3-yloxy)-phenylamino]-quinazolin-6-yl}-prop-2-ynyl)-amide | A | 465.2 | 4.21 |
| 191 | (±)-Azetidine-2-carboxylic acid (3-{4-[3-methyl-4-(6-methyl-pyridin-3-yloxy)-phenylamino]-quinazolin-6-yl}-prop-2-ynyl)-amide | A | 479.3 | 4.41 |
| 192 | (±)-Azetidine-2-carboxylic acid (3-{4-[3-chloro-4-(6-methyl-pyridin-3-yloxy)-phenylamino]-quinazolin-6-yl}-prop-2-ynyl)-amide | A | 499.3 | 4.70 |
| 193 | 1-Hydroxy-cyclopropanecarboxylic acid (3-{4-[3-methyl-4-(6-methyl-pyridin-3-yloxy)-phenylamino]-quinazolin-6-yl}-prop-2-ynyl)-amide | B | 480.0 | 5.20 |

TABLE I-continued

| Example No. | Name | Method | LRMS | HPLC RT |
|---|---|---|---|---|
| 194 | N-(3-{4-[3-Methyl-4-(6-methyl-pyridin-3-yloxy)-phenylamino]-quinazolin-6-yl}-prop-2-ynyl)-propionamide | B | 452.1 | 5.55 |
| 195 | N-(3-{4-[3-Methyl-4-(6-methyl-pyridin-3-yloxy)-phenylamino]-quinazolin-6-yl}-prop-2-ynyl)-butyramide | B | 466.1 | 5.88 |
| 196 | N-(3-{4-[3-Methyl-4-(6-methyl-pyridin-3-yloxy)-phenylamino]-quinazolin-6-yl}-prop-2-ynyl)-isobutyramide | B | 466.1 | 5.88 |
| 197 | 2-Ethoxy-N-(3-{4-[3-methyl-4-(6-methyl-pyridin-3-yloxy)-phenylamino]-quinazolin-6-yl}-prop-2-ynyl)-acetamide | B | 482.1 | 5.89 |
| 198 | N-(3-{4-[3-Methyl-4-(6-methyl-pyridin-3-yloxy)-phenylamino]-quinazolin-6-yl}-prop-2-ynyl)-2-methylsulfanyl-acetamide | B | 484.0 | 5.76 |
| 199 | Cyclopropanecarboxylic acid (3-{4-[3-methyl-4-(6-methyl-pyridin-3-yloxy)-phenylamino]-quinazolin-6-yl}-prop-2-ynyl)-amide | B | 464.1 | 5.76 |
| 200 | Cyclobutanecarboxylic acid (3-{4-[3-methyl-4-(6-methyl-pyridin-3-yloxy)-phenylamino]-quinazolin-6-yl}-prop-2-ynyl)-amide | B | 478.1 | 6.07 |
| 201 | [6-(3-Amino-prop-1-ynyl)-quinazolin-4-yl]-[3-methyl-4-(pyridin-3-yloxy)-phenyl]-amine | A | 382.1 | 4.02 |
| 202 | Isoxazole-5-carboxylic acid (3-{4-[3-methyl-4-(6-methyl-pyridin-3-yloxy)-phenylamino]-quinazolin-6-yl}-prop-2-ynyl)-amide | B | 491.0 | 5.78 |
| 203 | N-Methyl-N-(3-{4-[3-methyl-4-(6-methyl-pyridin-3-yloxy)-phenylamino]-quinazolin-6-yl}-prop-2-ynyl)-acetamide | B | 452.5 | 5.79 |
| 204 | 2-Methoxy-N-(1-methyl-3-{4-[3-methyl-4-(6-methyl-pyridin-3-yloxy)-phenylamino]-quinazolin-6-yl}-prop-2-ynyl)-acetamide | B | 481.9 | 5.86 |
| 205 | N-(1,1-Dimethyl-3-{4-[3-methyl-4-(6-methyl-pyridin-3-yloxy)-phenylamino]-quinazolin-6-yl}-prop-2-ynyl)-acetamide | B | 466.2 | 5.82 |
| 206 | 2R-Hydroxy-N-(3-{4-[3-methyl-4-(6-methyl-pyridin-3-yloxy)-phenylamino]-quinazolin-6-yl}-prop-2-ynyl)-propionamide | B | 468.0 | 4.95 |
| 207 | E-Cyclopropanecarboxylic acid (3-{4-[3-methyl-4-(6-methyl-pyridin-3-yloxy)-phenylamino]-quinazolin-6-yl}-allyl)-amide | G | 466.1 | 5.41 |
| 208 | E-N-(3-{4-[3-Methyl-4-(6-methyl-pyridin-3-yloxy)-phenylamino]-quinazolin-6-yl}-allyl)-propionamide | G | 454.1 | 5.07 |
| 209 | E-2-Ethoxy-N-(3-{4-[3-methyl-4-(6-methyl-pyridin-3-yloxy)-phenylamino]-quinazolin-6-yl}-allyl)-acetamide | G | 484.0 | 5.54 |
| 210 | E-(±)-2-Methoxy-N-(3-{4-[3-methyl-4-(6-methyl-pyridin-3-yloxy)-phenylamino]-quinazolin-6-yl}-allyl)-propionamide | G | 484.1 | 5.45 |
| 211 | E-2-Fluoro-N-(3-{4-[3-methyl-4-(6-methyl-pyridin-3-yloxy)-phenylamino]-quinazolin-6-yl}-allyl)-acetamide | G | 458.1 | 5.48 |
| 212 | 2-Methoxy-N-(1-{4-[3-methyl-4-(6-methyl-pyridin-3-yloxy)-phenylamino]-quinazolin-6-ylethynyl}-cyclobutyl)-acetamide | B | 508.0 | 6.17 |
| 213 | N-(1-{4-[3-Methyl-4-(6-methyl-pyridin-3-yloxy)-phenylamino]-quinazolin-6-ylethynyl}-cyclobutyl)-acetamide | B | 478.0 | 5.90 |
| 214 | E-N-(3-{4-[3-Chloro-4-(6-methyl-pyridin-3-yloxy)-phenylamino]-quinazolin-6-yl}-allyl)-2-fluoro-acetamide | G | 478.0 | 5.55 |
| 215 | E-Cyclopropanecarboxylic acid (3-{4-[3-chloro-4-(6-methyl-pyridin-3-yloxy)-phenylamino]-quinazolin-6-yl}-allyl)-amide | G | 485.7 | 5.77 |
| 216 | [6-(1-Amino-cyclobutylethynyl)-quinazolin-4-yl]-[3-methyl-4-(6-methyl-pyridin-3-yloxy)-phenyl]-amine | A | 436.0 | 4.87 |
| 217 | (±)-2-Methoxymethyl-pyrrolidine-1-carboxylic acid (3-{4-[3-methyl-4 (6-methyl-pyridin-3-yloxy)-phenylamino]-quinazolin-6-yl}-prop-2-ynyl)-amide | D | 537.1 | 6.13 |

TABLE I-continued

| Example No. | Name | Method | LRMS | HPLC RT |
|---|---|---|---|---|
| 218 | Piperazine-1-carboxylic acid (3-{4-[3-methyl-4-(6-methyl-pyridin-3-yloxy)-phenylamino]-quinazolin-6-yl}-prop-2-ynyl)-amide | D | 508.1 | 4.28 |
| 219 | 3-(3-{4-[3-Chloro-4-(6-methyl-pyridin-3-yloxy)-phenylamino]-quinazolin-6-yl}-prop-2-ynyl)-1-ethyl-1-(2-hydroxy-ethyl)-urea | D | 531.0 | 5.41 |
| 220 | [6-(1-Amino-cyclopropylethynyl)-quinazolin-4-yl]-[3-methyl-4-(6-methyl-pyridin-3-yloxy)-phenyl]-amine | A | 422.1 | 5.11 |
| 221 | E-3-{4-[3-Methyl-4-(6-methyl-pyridin-3-yloxy)-phenylamino]-quinazolin-6-yl}-prop-2-en-1-ol | E | 399.2 | 4.93 |
| 222 | N-(3-{4-[3-Chloro-4-(6-methyl-pyridin-3-yloxy)-phenylamino]-quinazolin-6-yl}-prop-2-ynyl)-2-(2-methoxy-ethoxy)-acetamide | B | 532.0 | 5.86 |
| 223 | N-(3-{4-[3-Chloro-4-(6-methyl-pyridin-3-yloxy)-phenylamino]-quinazolin-6-yl}-prop-2-ynyl)-2-oxo-propionamide | B | 486.0 | 6.17 |
| 224 | N-(3-{4-[3-Chloro-4-(6-methyl-pyridin-3-yloxy)-phenylamino]-quinazolin-6-yl}-prop-2-ynyl)-2-(2-hydroxy-ethylsulfanyl)-acetamide | C | 534.0 | 5.57 |
| 225 | N-(3-{4-[3-Chloro-4-(6-methyl-pyridin-3-yloxy)-phenylamino]-quinazolin-6-yl}-prop-2-ynyl)-2-methylsulfanyl-acetamide | B | 504.0 | 6.04 |
| 226 | Pyrrolidine-2R-carboxylic acid (3-{4-[3-chloro-4-(6-methyl-pyridin-3-yloxy)-phenylamino]-quinazolin-6-yl}-prop-2-ynyl)-amide | A | 513.4 | 4.86 |
| 227 | Pyrrolidine-2R-carboxylic acid (3-{4-[3-chloro-4-(pyridin-3-yloxy)-phenylamino]-quinazolin-6-yl}-prop-2-ynyl)-amide | A | 499.0 | 4.45 |
| 228 | (±)-2-Methanesulfinyl-N-(3-{4-[3-methyl-4-(pyridin-3-yloxy)-phenylamino]-quinazolin-6-yl}-prop-2-ynyl)-acetamide | B | 486.1 | 4.52 |
| 229 | (±)-2-Methanesulfinyl-N-(3-{4-[3-Chloro-4-(pyridin-3-yloxy)-phenylamino]-quinazolin-6-yl}-prop-2-ynyl)-acetamide | B | 506.0 | 4.81 |
| 230 | (±)-Tetrahydro-furan-3-carboxylic acid (3-{4-[3-methyl-4-(pyridin-3-yloxy)-phenylamino]-quinazolin-6-yl}-prop-2-ynyl)-amide | B | 480.1 | 5.11 |
| 231 | 2-Hydroxy-N-(3-{4-[3-methyl-4-(pyridin-3-yloxy)-phenylamino]-quinazolin-6-yl}-prop-2-ynyl)-acetamide | A | 440.3 | 4.60 |
| 232 | 2-Ethoxy-N-(3-{4-[3-methyl-4-(pyridin-3-yloxy)-phenylamino]-quinazolin-6-yl}-prop-2-ynyl)-acetamide | B | 467.9 | 5.62 |
| 233 | [3-Methyl-4-(pyridin-3-yloxy)-phenyl]-(6-piperidin-4-ylethynyl-quinazolin-4-yl)-amine | A | 436.6 | 4.35 |
| 234 | Cyclobutanecarboxylic acid (3-{4-[3-methyl-4-(pyridin-3-yloxy)-phenylamino]-quinazolin-6-yl}-prop-2-ynyl)-amide | B | 464.0 | 5.78 |
| 235 | Cyclopropanecarboxylic acid (3-{4-[3-methyl-4-(pyridin-3-yloxy)-phenylamino]-quinazolin-6-yl}-prop-2-ynyl)-amide | B | 450.0 | 5.44 |
| 236 | [3-Methyl-4-(pyridin-2-yloxy)-phenyl]-(6-piperidin-3-ylethynyl-quinazolin-4-yl)-amine | A | 436.0 | 4.64 |
| 237 | (6-Azetidin-3-ylethynyl-quinazolin-4-yl)-[3-methyl-4-(pyridin-3-yloxy)-phenyl]-amine | A | 407.9 | 4.10 |
| 238 | N-(1,1-Dimethyl-3-{4-[3-methyl-4-(pyridin-3-yloxy)-phenylamino]-quinazolin-6-yl}-prop-2-ynyl)-2-methoxy-acetamide | B | 481.9 | 5.96 |
| 239 | 2-[4-(3-{4-[3-Methyl-4-(pyridin-3-yloxy)-phenylamino]-quinazolin-6-yl}-prop-2-ynyl)-piperazin-1-yl]-ethanol | A | 495.4 | 4.10 |
| 240 | (±)-2-Methoxy-N-(1-methyl-3-{4-[3-methyl-4-(pyridin-3-yloxy)-phenylamino]-quinazolin-6-yl}-prop-2-ynyl)-acetamide | B | 467.9 | 5.57 |
| 241 | [3-Methyl-4-(pyridin-3-yloxy)-phenyl]-(6-piperidin-3R-ylethynyl-quinazolin-4-yl)-amine | A | 436.0 | 4.48 |

TABLE I-continued

| Example No. | Name | Method | LRMS | HPLC RT |
|---|---|---|---|---|
| 242 | [3-Methyl-4-(pyridin-3-yloxy)-phenyl]-(6-piperidin-3S-ylethynyl-quinazolin-4-yl)-amine | A | 436.0 | 4.48 |
| 243 | (±)-[3-Methyl-4-(pyridin-3-yloxy)-phenyl]-(6-pyrrolidin-3-ylethynyl-quinazolin-4-yl)-amine | A | 422.0 | 4.30 |

TABLE II

| Example No. | Name | Method | LRMS | HPLC RT |
|---|---|---|---|---|
| 244 | 1-(2-Methoxy-ethyl)-1-methyl-3-(3-{4-[3-methyl-4-(6-methyl-pyridin-3-yloxy)-phenylamino]-quinazolin-6-yl}-prop-2-ynyl)-urea | D | 511.1 | 5.61 |
| 245 | (±)-2-Hydroxymethyl-pyrrolidine-1-carboxylic acid (3-{4-[3-methyl-4-(6-methyl-pyridin-3-yloxy)-phenylamino]-quinazolin-6-yl}-prop-2-ynyl)-amide | D | 523.1 | 5.19 |
| 246 | (±)-3-Hydroxy-pyrrolidine-1-carboxlic acid (3-{4-[3-methyl-4-(6-methyl-pyridin-3-yloxy)-phenylamino]-quinazolin-6-yl}-prop-2-ynyl)-amide | D | 509.1 | 4.75 |
| 247 | Cis- and trans-2,5-Dimethyl-pyrrolidine-1-carboxylic acid (3-{4-[3-methyl-4-(6-methyl-pyridin-3-yloxy)-phenylaminio]-quinazolin-6-yl}-prop-2-ynyl)-amide | D | 521.1 | 6.38, 6.28 |
| 248 | 1-Isobutyl-1-methyl-3-(3-{4-[3-methyl-4-(6-methyl-pyridin-3-yloxy)-phenylamino]-quinazolin-6-yl}-prop-2-ynyl)-urea | D | 509.1 | 6.45 |
| 249 | N-(1-{4-[3-Methyl-4-(6-methyl-pyridin-3-yloxy)-phenylamino]-quinazolin-6-ylethynyl}-cyclopropyl)-acetamide | B | 464.0 | 5.46 |
| 250 | 2-Methoxy-N-(1-{4-[3-methyl-4-(6-methyl-pyridin-3-yloxy)-phenylamino]-quinazolin-6-ylethynyl}-cyclopropyl)-acetamide | B | 5.76 | 493.7 |
| 251 | E-N-(3-{4-[3-Chloro-4-(6-methyl-pyridin-3-yloxy)-phenylamino]-quinazolin-6-yl}-allyl)-propionamide | G | 474.0 | 5.53 |
| 252 | E-N-(3-{4-[3-Chloro-4-(6-methyl-pyridin-3-yloxy)-phenylamino]-quinazolin-6-yl}-allyl)-2-methoxy-propionamide | G | 504.0 | 5.67 |
| 253 | E-N-(3-{4-[3-Chloro-4-(6-methyl-pyridin-3-yloxy)-phenylamino]-quinazolin-6-yl}-allyl)-2-methoxy-acetamide | G | 489.7 | 5.52 |
| 254 | E-N-(3-{4-[3-Chloro-4-(6-methyl-pyridin-3-yloxy)-phenylamino]-quinazolin-6-yl}-allyl)-2-ethoxy-acetamide | G | 504.0 | 5.89 |
| 255 | (3-{4-[3-Methyl-4-(6-methyl-pyridin-3-yloxy)-phenylamino]-quinazolin-6-yl}-prop-2-ynyl)-carbamic acid tert-butyl ester | B | 496.3 | 7.11 |
| 256 | 2-(R)-Hydroxy-N-(3-{4-[3-methyl-4-(6-methyl-pyridin-3-yloxy)-phenylamino]-quinazolin-6-yl}-prop-2-ynyl)-propionamide | B | 468.0 | 5.04 |
| 257 | Cyclobutanecarboxylic acid (3-{4-[3-chloro-4-(6-methyl-pyridin-3-yloxy)-phenylamino]-quinazolin-6-yl}-prop-2-ynyl)-amide | B | 498.0, 500.0 | 6.36 |
| 258 | N-(3-{4-[3-Chloro-4-(6-methyl-pyridin-3-yloxy)-phenylamino]-quinazolin-6-yl}-prop-2-ynyl)-propionamide | B | 472.0, 474.0 | 5.86 |
| 259 | Cyclopropanecarboxylic acid (3-{4-[3-chloro-4-(6-methyl-pyridin-3-yloxy)-phenylamino]-quinazolin-6-yl}-prop-2-ynyl)-amide | B | 484.0, 486.0 | 6.06 |
| 260 | N-(3-{4-[3-Chloro-4-(6-methyl-pyridin-3-yloxy)-phenylamino]-quinazolin-6-yl}-prop-2-ynyl)-isobutyramide | B | 486.1, 488.1 | 6.17 |

TABLE II-continued

| Example No. | Name | Method | LRMS | HPLC RT |
|---|---|---|---|---|
| 261 | (±)-N-(3-{4-[3-Chloro-4-(6-methyl-pyridin-3-yloxy)-phenylamino]-quinazolin-6-yl}-prop-2-ynyl)-2-methoxy-propionamide | B | 502.0, 504.0 | 6.00 |
| 262 | (±)-2-Methoxy-N-(3-{4-[3-methyl-4-(6-methyl-pyridin-3-yloxy)-phenylamino]-quinazolin-6-yl}-prop-2-ynyl)-propionamide | B | 482.1 | 5.73 |
| 263 | 5-Oxo-pyrrolidine-2R-carboxylic acid (3-{4-[3-methyl-4-(6-methyl-pyridin-3-yloxy)-phenylamino]-quinazolin-6-yl}-prop-2-ynyl)-amide | B | 507.1 | 4.73 |
| 264 | E-1-Hydroxy-cyclopropanecarboxylic acid (3-{4-[3-methyl-4-(6-methyl-pyridin-3-yloxy)-phenylamino]-quinazolin-6-yl}-allyl)-amide | I | 482.0 | 4.65 |
| 265 | E-2S-Hydroxy-N-(3-{4-[3-methyl-4-(6-methyl-pyridin-3-yloxy)-phenylamino]-quinazolin-6-yl}-allyl)-propionamide | I | 470.1 | 4.56 |
| 266 | E-2R-Hydroxy-N-(3-{4-[3-methyl-4-(6-methyl-pyridin-3-yloxy)-phenylamino]-quinazolin-6-yl}-allyl)-propionamide | I | 470.1 | 4.60 |
| 267 | E-2-Hydroxy-N-(3-{4-[3-methyl-4-(6-methyl-pyridin-3-yloxy)-phenylamino]-quinazolin-6-yl}-allyl)-acetamide | I | 456.1 | 4.51 |
| 268 | 1-Cyanomethyl-3-(3-{4-[3-methyl-4-(6-methyl-pyridin-3-yloxy)-phenylamino]-quinazolin-6-yl}-prop-2-ynyl)-urea | D | 478.1 | 5.26 |
| 269 | 1-Cyclobutyl-3-(3-{4-[3-methyl-4-(6-methyl-pyridin-3-yloxy)-phenylamino]-quinazolin-6-yl}-prop-2-ynyl)-urea | D | 492.8 | 5.90 |
| 270 | 1,1,3-Trimethyl-3-(3-{4-[3-methyl-4-(6-methyl-pyridin-3-yloxy)-phenylamino]-quinazolin-6-yl}-prop-2-ynyl)-urea | D | 481.1 | 6.30 |
| 271 | 1-(3-{4-[3-Chloro-4-(6-methyl-pyridin-3-yloxy)-phenylamino]-quinazolin-6-yl}-prop-2-ynyl)-1,3,3-trimethyl-urea | D | 501.1 | 6.52 |
| 272 | 1-Ethyl-1-(2-hydroxy-ethyl)-3-(3-{4-[3-methyl-4-(6-methyl-pyridin-3-yloxy)-phenylamino]-quinazolin-6-yl}-prop-2-ynyl)-urea | D | 511.1 | 5.20 |
| 273 | (±)-3-Dimethylamino-pyrrolidine-1-carboxylic acid (3-{4-[3-methyl-4-(6-methyl-pyridin-3-yloxy)-phenylamino]-quinazolin-6-yl}-prop-2-ynyl)-amide | D | 536.1 | 4.40 |
| 274 | Morpholine-4-carboxylic acid (1-methyl-3-{4-[3-methyl-4-(6-methyl-pyridin-3-yloxy)-phenylamino]-quinazolin-6-yl}-prop-2-ynyl)-amide | D | 523.4 | 5.58 |
| 275 | Exo-6-Amino-3-aza-bicyclo[3.1.0]hexane-3-carboxylic acid (3-{4-[3-methyl-4-(6-methyl-pyridin-3-yloxy)-phenylamino]-quinazolin-6-yl}-prop-2-ynyl)-amide | D | 520.9 | 4.28 |
| 276 | Exo-6-Hydroxymethyl-3-aza-bicyclo[3.1.0]hexane-3-carboxylic acid (3-{4-[3-methyl-4-(6-methyl-pyridin-3-yloxy)-phenylamino]-quinazolin-6-yl}-prop-2-ynyl)-amide | D | 535.1 | 4.98 |
| 277 | (3-{4-[3-Methyl-4-(6-methyl-pyridin-3-yloxy)-phenylamino]-quinazolin-6-yl}-prop-2-ynyl)-urea | D | 439.8 | 4.81 |
| 278 | E-N-(3-{4-[3-Chloro-4-(6-methyl-pyridin-3-yloxy)-phenylamino]-quinazolin-6-yl}-allyl)-2-hydroxy-acetamide | I | 476.0 | 4.86 |
| 279 | Piperazine-1-carboxylic acid (1,1-dimethyl-3-{4-[3-methyl-4-(6-methyl-pyridin-3-yloxy)-phenylamino]-quinazolin-6-yl}-prop-2-ynyl)-amide | D | 536.1 | 4.74 |
| 280 | 1-(1,1-Dimethyl-3-{4-[3-methyl-4-(6-methyl-pyridin-3-yloxy)-phenylamino]-quinazolin-6-yl}-prop-2-ynyl)-3-ethyl-urea | D | 495.3 | 6.11 |

TABLE II-continued

| Example No. | Name | Method | LRMS | HPLC RT |
|---|---|---|---|---|
| 281 | Morpholine-4-carboxylic acid (1,1-dimethyl-3-{4-[3-methyl-4-(6-methyl-pyridin-3-yloxy)-phenylamino]-quinazolin-6-yl}-prop-2-ynyl)-amide | D | 537.3 | 6.02 |
| 282 | 1,3-Dimethyl-1-(3-{4-[3-methyl-4-(6-methyl-pyridin-3-yloxy)-phenylamino]-quinazolin-6-yl}-prop-2-ynyl)-urea | D | 467.1 | 5.51 |
| 283 | N-(3-{4-[3-Chloro-4-(6-methyl-pyridin-3-yloxy)-phenylamino]-quinazolin-6-yl}-1,1-dimethyl-prop-2-ynyl)-2-hydroxy-acetamide | B | 5.02, 5.04 | 5.74 |
| 284 | N-(1,1-Dimethyl-3-{4-[3-methyl-4-(6-methyl-pyridin-3-yloxy)-phenylamino]-quinazolin-6-yl}-prop-2-ynyl)-2-hydroxy-acetamide | B | 482.2 | 5.46 |
| 285 | E-1,1-Diethyl-3-(3-{4-[3-methyl-4-(6-methyl-pyridin-3-yloxy)-phenylamino]-quinazolin-6-yl}-allyl)-urea | H | 497.1 | 5.72 |
| 286 | E-pyrrolidine-1-carboxylic acid (3-{4-[3-methyl-4-(6-methyl-pyridin-3-yloxy)-phenylamino]-quinazolin-6-yl}-allyl)-amide | H | 495.1 | 5.40 |
| 287 | E-1-Ethyl-3-(3-{4-[3-methyl-4-(6-methyl-pyridin-3-yloxy)-phenylamino]-quinazolin-6-yl}-allyl)-urea | H | 469.1 | 4.80 |
| 288 | E-Morpholine-4-carboxylic acid (3-{4-[3-methyl-4-(6-methyl-pyridin-3-yloxy)-phenylamino]-quinazolin-6-yl}-allyl)-amide | H | 511.1 | 4.75 |
| 289 | (±)-1-Ethyl-1-(2-hydroxy-ethyl)-3-(1-methyl-3-{4-[3-methyl-4-(6-methyl-pyridin-3-yloxy)-phenylamino]-quinazolin-6-yl}-prop-2-ynyl)-urea | D | 525.1 | 5.51 |
| 290 | (±)-1-Ethyl-3-(1-methyl-3-{4-[3-methyl-4-(6-methyl-pyridin-3-yloxy)-phenylamino]-quinazolin-6-yl}-prop-2-ynyl)-urea | D | 481.1 | 5.68 |
| 291 | 4-Methyl-piperazine-1-carboxylic acid (3-{4-[3-methyl-4-(6-methyl-pyridin-3-yloxy)-phenylamino]-quinazolin-6-yl}-prop-2-ynyl)-amide | D | 522.3 | 4.44 |
| 292 | N-(3-{4-[3-Chloro-4-(6-methyl-pyridin-3-yloxy)-phenylamino]-quinazolin-6-yl}-prop-2-ynyl)-2-cyano-acetamide | B | 483.1 | 5.73 |
| 293 | 2-Cyano-N-(3-{4-[3-methyl-4-(6-methyl-pyridin-3-yloxy)-phenylamino]-quinazolin-6-yl}-prop-2-ynyl)-acetamide | B | 463.1 | 5.44 |
| 294 | E-N-(3-{4-[3-Methyl-4-(6-methyl-pyridin-3-yloxy)-phenylamino]-quinazolin-6-yl}-allyl)-2-methylsulfanyl-acetamide | G | 486.3 | 5.33 |
| 295 | E-5-Oxo-tetrahydro-furan-2R-carboxylic acid (3-{4-[3-methyl-4-(6-methyl-pyridin-3-yloxy)-phenylamino]-quinazolin-6-yl}-allyl)-amide | G | 510.2 | 5.58 |
| 296 | E-N-(3-{4-[3-Methyl-4-(6-methyl-pyridin-3-yloxy)-phenylamino]-quinazolin-6-yl}-allyl)-methanesulfonamide | G | 476.0 | 5.36 |
| 297 | (±)-5-{4-[3-Methyl-4-(6-methyl-pyridin-3-yloxy)-phenylamino]-quinazolin-6-ylethynyl}-morpholin-3-one | B | 466.1 | 5.22 |
| 298 | E-N-(3-{4-[3-Chloro-4-(6-methyl-pyridin-3-yloxy)-phenylamino]-quinazolin-6-yl}-allyl)-2S-hydroxy-propionamide | I | 490.1 | 5.06 |
| 299 | E-1-Hydroxy-cyclopropanecarboxylic acid (3-{4-[3-chloro-4-(6-methyl-pyridin-3-yloxy)-phenylamino]-quinazolin-6-yl}-allyl)-amide | I | 502.2 | 5.24 |
| 300 | E-N-(3-{4-[3-Chloro-4-(6-methyl-pyridin-3-yloxy)-phenylamino]-quinazolin-6-yl}-allyl)-2-hydroxy-isobutyramide | I | 504.2 | 5.24 |
| 301 | (±)-E-N-(3-{4-[3-Chloro-4-(6-methyl-pyridin-3-yloxy)-phenylamino]-quinazolin-6-yl}-allyl)-2-hydroxy-propionamide | I | 490.0 | 5.07 |

TABLE II-continued

| Example No. | Name | Method | LRMS | HPLC RT |
|---|---|---|---|---|
| 302 | 2R-Amino-N-(3-{4-[3-chloro-4-(6-methyl-pyridin-3-yloxy)-phenylamino]-quinazolin-6-yl}-prop-2-ynyl)-propionamide | A | 487.1 | 4.54 |
| 303 | 2R-Amino-N-(3-{4-[3-methyl-4-(6-methyl-pyridin-3-yloxy)-phenylamino]-quinazolin-6-yl}-prop-2-ynyl)-propionamide | A | 467.2 | 4.35 |
| 304 | (±)-4-{4-[3-Methyl-4-(6-methyl-pyridin-3-yloxy)-phenylamino]-quinazolin-6-ylethynyl}-oxazolidin-2-one | | 452.2 | 5.40 |
| 305 | (±)-E-3,3,3-Trifluoro-2-hydroxy-N-(3-{4-[3-methyl-4-(6-methyl-pyridin-3-yloxy)-phenylamino]-quinazolin-6-yl}-allyl)-propionamide | I | 524.1 | 5.52 |
| 306 | (±)-E-2-Hydroxy-3-methyl-N-(3-{4-[3-methyl-4-(6-methyl-pyridin-3-yloxy)-phenylamino]-quinazolin-6-yl}-allyl)-butyramide | I | 498.2 | 5.49 |
| 307 | (±)-2-Methoxymethyl-pyrrolidine-1-carboxylic acid (3-{4-[3-chloro-4-(6-methyl-pyridin-3-yloxy)-phenylamino]-quinazolin-6-yl}-prop-2-ynyl)-amide | D | 557.1 | 6.42 |
| 308 | (±)-2-Hydroxymethyl-pyrrolidine-1-carboxylic acid (3-{4-[3-chloro-4-(6-methyl-pyridin-3-yloxy)-phenylamino]-quinazolin-6-yl}-prop-2-ynyl)-amide | D | 543.2 | 5.61 |
| 309 | (±)-1-(3-{4-[3-Chloro-4-(6-methyl-pyridin-3-yloxy)-phenylamino]-quinazolin-6-yl}-prop-2-ynyl)-3-(1,2-dimethyl-propyl)-urea | D | 529.2 | 6.87 |
| 310 | (±)-1-(3-{4-[3-Chloro-4-(6-methyl-pyridin-3-yloxy)-phenylamino]-quinazolin-6-yl}-prop-2-ynyl)-3-(1,1-dimethyl-propyl)-urea | D | 529.2 | 6.89 |
| 311 | (±)-1-(3-{4-[3-Chloro-4-(6-methyl-pyridin-3-yloxy)-phenylamino]-quinazolin-6-yl}-prop-2-ynyl)-3-(1-hydroxymethyl-propyl)-urea | D | 531.1 | 5.41 |
| 312 | 1-(3-{4-[3-Chloro-4-(6-methyl-pyridin-3-yloxy)-phenylamino]-quinazolin-6-yl}-prop-2-ynyl)-3-(1-ethyl-propyl)-urea | D | 529.1 | 6.63 |
| 313 | (±)-1-sec-Butyl-3-(3-{4-[3-chloro-4-(6-methyl-pyridin-3-yloxy)-phenylamino]-quinazolin-6-yl}-prop-2-ynyl)-urea | D | 515.1 | 6.32 |
| 314 | (±)-1-(1,1-Dimethyl-propyl)-3-(3-{4-[3-methyl-4-(6-methyl-pyridin-3-yloxy)-phenylamino]-quinazolin-6-yl}-prop-2-ynyl)-urea | D | 509.2 | 6.60 |
| 315 | (±)-1-(1-Hydroxymethyl-propyl)-3-(3-{4-[3-methyl-4-(6-methyl-pyridin-3-yloxy)-phenylamino]-quinazolin-6-yl}-prop-2-ynyl)-urea | D | 511.2 | 5.13 |
| 316 | 1-(1-Ethyl-propyl)-3-(3-{4-[3-methyl-4-(6-methyl-pyridin-3-yloxy)-phenylamino]-quinazolin-6-yl}-prop-2-ynyl)-urea | D | 509.3 | 6.35 |
| 317 | (±)-1-sec-Butyl-3-(3-{4-[3-methyl-4-(6-methyl-pyridin-3-yloxy)-phenylamino]-quinazolin-6-yl}-prop-2-ynyl)-urea | D | 495.3 | 6.07 |
| 318 | Azetidine-1-carboxylic acid (3-{4-[3-methyl-4-(6-methyl-pyridin-3-yloxy)-phenylamino]-quinazolin-6-yl}-prop-2-ynyl)-amide | D | 479.2 | 5.46 |
| 319 | 1-(1,2-Dimethyl-propyl)-3-(3-{4-[3-methyl-4-(6-methyl-pyridin-3-yloxy)-phenylamino]-quinazolin-6-yl}-prop-2-ynyl)-urea | D | 509.2 | 6.36 |
| 320 | Piperidine-1-carboxylic acid (3-{4-[3-methyl-4-(6-methyl-pyridin-3-yloxy)-phenylamino]-quinazolin-6-yl}-prop-2-ynyl)-amide | D | 507.3 | 6.21 |
| 321 | E-Pyridine-2-carboxylic acid (3-{4-[3-methyl-4-(6-methyl-pyridin-3-yloxy)-phenylamino]-quinazolin-6-yl}-allyl)-amide | G | 503.3 | 6.11 |

TABLE II-continued

| Example No. | Name | Method | LRMS | HPLC RT |
|---|---|---|---|---|
| 322 | E-2-Isopropoxy-N-(3-{4-[3-methyl-4-(6-methyl-pyridin-3-yloxy)-phenylamino]-quinazolin-6-yl}-allyl)-acetamide | G | 498.3 | 5.94 |
| 323 | E-N-(3-{4-[3-Methyl-4-(6-methyl-pyridin-3-yloxy)-phenylamino]-quinazolin-6-yl}-allyl)-benzenesulfonamide | G | 538.1 | 6.51 |
| 324 | E-Ethanesulfonic acid (3-{4-[3-methyl-4-(6-methyl-pyridin-3-yloxy)-phenylamino]-quinazolin-6-yl}-allyl)-amide | G | 490.3 | 5.62 |
| 325 | E-1H-Imidazole-4-carboxylic acid (3-{4-[3-methyl-4-(6-methyl-pyridin-3-yloxy)-phenylamino]-quinazolin-6-yl}-allyl)-amide | G | 492.3 | 5.53 |
| 326 | E-Isoxazole-5-carboxylic acid (3-{4-[3-methyl-4-(6-methyl-pyridin-3-yloxy)-phenylamino]-quinazolin-6-yl}-allyl)-amide | G | 493.2 | 5.41 |
| 327 | E-Pyrrolidine-1-carboxylic acid (3-{4-[3-chloro-4-(6-methyl-pyridin-3-yloxy)-phenylamino]-quinazolin-6-yl}-allyl)-amide | H | 515.2 | 5.77 |
| 328 | E-Morpholine-4-carboxylic acid (3-{4-[3-chloro-4-(6-methyl-pyridin-3-yloxy)-phenylamino]-quinazolin-6-yl}-allyl)-amide | H | 531.1 | 5.20 |
| 329 | E-N-(3-{4-[3-Chloro-4-(6-methyl-pyridin-3-yloxy)-phenylamino]-quinazolin-6-yl}-allyl)-2-methylsulfanyl-acetamide | G | 506.1 | 5.81 |
| 330 | E-5-Oxo-tetrahydro-furan-2R-carboxylic acid (3-{4-[3-chloro-4(6-methyl-Pyridin-3-yloxy)-phenylamino]-quinazolin-6-yl}-allyl)-amide | G | 530.2 | 5.44 |
| 331 | E-N-(3-{4-[3-Chloro-4-(6-methyl-Pyridin-3-yloxy)-phenylamino]-quinazolin-6-yl}-allyl)-2-cyclopropylmethoxy-acetamide | G | 530.2 | 6.34 |
| 332 | (±)-E-N-(3-{4-[3-Chloro-4-(6-methyl-pyridin-3-yloxy)-phenylamino]-quinazolin-6-yl}-allyl)-2-hydroxy-3-methyl-butyramide | I | 518.2 | 5.73 |
| 333 | E-N-(3-{4-[3-Chloro-4-(6-methyl-pyridin-3-yloxy)-phenylamino]-quinazolin-6-yl}-allyl)-methanesulfonamide | G | 496.1 | 5.72 |
| 334 | E-2R-Hydroxymethyl-pyrrolidine-1-carboxylic acid (3-{4-[3-methyl-4-(6-methyl-pyridin-3-yloxy)-phenylamino]-quinazolin-6-yl}-allyl)-amide | H | 525.2 | 4.91 |
| 335 | E-2S-Hydroxymethyl-pyrrolidine-1-carboxylic acid (3-{4-[3-methyl-4-(6-methyl-pyridin-3-yloxy)-phenylamino]-quinazolin-6-yl}-allyl)-amide | H | 525.2 | 4.92 |
| 336 | E-2-Cyclopropylmethoxy-N-(3-{4-[3-methyl-4-(6-methyl-pyridin-3-yloxy)-phenylamino]-quinazolin-6-yl}-allyl)-acetamide | G | 510.3 | 6.00 |
| 337 | E-1-Isopropyl-3-(3-{4-[3-methyl-4-(6-methyl-pyridin-3-yloxy)-phenylamino]-quinazolin-6-yl}-allyl)-urea | H | 483.2 | 5.33 |
| 338 | Azetidine-1-carboxylic acid (3-{4-[3-chloro-4-(6-methyl-pyridin-3-yloxy)-phenylamino]-quinazolin-6-yl}-prop-2-ynyl)-amide | D | 499.2 | 5.73 |
| 339 | Piperazine-1-carboxylic acid (3-{4-[3-chloro-4-(6-methyl-pyridin-3-yloxy)-phenylamino]-quinazolin-6-yl}-prop-2-ynyl)-amide | D | 528.2 | 4.65 |
| 340 | 2-Methoxy-N-(3-{7-methoxy-4-[3-methyl-4-(6-methyl-pyridin-3-yloxy)-phenylamino]-quinazolin-6-yl}-prop-2-ynyl)-acetamide | B | 498.2 | 5.47 |
| 341 | N-(3-{4-[3-Chloro-4-(6-methyl-pyridin-3-yloxy)-phenylamino]-7-methoxy-quinazolin-6-yl}-prop-2-ynyl)-2-methoxy-acetamide | B | 518.2 | 5.76 |
| 342 | 3-(3-{4-[3-Chloro-4-(6-methyl-pyridin-3-yloxy)-phenylamino]-quinazolin-6-yl}- | D | 531.2 | 5.92 |

TABLE II-continued

| Example No. | Name | Method | LRMS | HPLC RT |
|---|---|---|---|---|
| | prop-2-ynyl)-1-(2-methoxy-ethyl)-1-methyl-urea | | | |
| 343 | N-(3-{7-Methoxy-4-[3-methyl-4-(6-methyl-pyridin-3-yloxy)-phenylamino]-quinazolin-6-yl}-prop-2-ynyl)-acetamide | B | 468.2 | 5.21 |
| 344 | N-(3-{4-[3-Chloro-4-(6-methyl-pyridin-3-yloxy)-phenylamino]-7-methoxy-quinazolin-6-yl}-prop-2-ynyl)-acetamide | B | 488.2 | 5.50 |
| 345 | 1,1-Diisopropyl-3-(3-{7-methoxy-4-[3-methyl-4-(6-methyl-pyridin-3-yloxy)-phenylamino]-quinazolin-6-yl}-prop-2-ynyl)-urea | D | 553.3 | 6.79 |
| 346 | (±)-2-Methyl-piperidine-1-carboxylic acid (3-{4-[3-methyl-4-(6-methyl-pyridin-3-yloxy)-phenylamino]-quinazolin-6-yl}-prop-2-ynyl)-amide | D | 521.3 | 6.53 |
| 347 | E-Azetidine-2S-carboxylic acid (3-{4-[3-methyl-4-(6-methyl-pyridin-3-yloxy)-phenylamino]-quinazolin-6-yl}-allyl)-amide | G | 481.3 | 4.10 |
| 348 | E-1-Amino-cyclopropanecarboxylic acid (3-{4-[3-methyl-4-(6-methyl-pyridin-3-yloxy)-phenylamino]-quinazolin-6-yl}-allyl)-amide | G | 481.3 | 4.40 |
| 349 | E-2-Amino-N-(3-{4-[3-methyl-4-(6-methyl-pyridin-3-yloxy)-phenylamino]-quinazolin-6-yl}-allyl)-isobutyramide | G | 483.3 | 4.12 |
| 350 | E-5-Oxo-pyrrolidine-2R-carboxylic acid (3-{4-[3-methyl-4-(6-methyl-pyridin-3-yloxy)-phenylamino]-quinazolin-6-yl}-allyl)-amide | G | 509.2 | 4.45 |
| 351 | E-2R-Amino-N-(3-{4-[3-methyl-4-(6-methyl-pyridin-3-yloxy)-phenylamino]-quinazolin-6-yl}-allyl)-propionamide | G | 469.3 | 4.09 |
| 352 | E-2S-Amino-N-(3-{4-[3-methyl-4-(6-methyl-pyridin-3-yloxy)-phenylamino]-quinazolin-6-yl}-allyl)-propionamide | G | 469.3 | 4.09 |
| 353 | E-5-Oxo-pyrrolidine-2R-carboxylic acid (3-{4-[3-methyl-4-(6-methyl-pyridin-3-yloxy)-phenylamino]-quinazolin-6-yl}-allyl)-amide | G | 509.2 | 4.42 |
| 354 | E-Isoxazole-5-carboxylic acid (3-{4-[3-chloro-4-(6-methyl-pyridin-3-yloxy)-phenylamino]-quinazolin-6-yl}-allyl)-amide | G | 513.0 | 5.86 |
| 355 | E-3-(3-{4-[3-Chloro-4-(6-methyl-pyridin-3-yloxy)-phenylamino]-quinazolin-6-yl}-allyl)-1,1-diethyl-urea | H | 517.2 | 6.11 |
| 356 | E-Pyridine-2-carboxylic acid (3-{4-[3-chloro-4-(6-methyl-pyridin-3-yloxy)-phenylamino]-quinazolin-6-yl}-allyl)-amide | G | 523.1 | 6.47 |
| 357 | N-(3-{4-[3-Methyl-4-(6-methyl-pyridin-3-yloxy)-phenylamino]-quinazolin-6-yl}-prop-2-ynyl)-methanesulfonamide | B | 474.2 | 5.66 |
| 358 | N-(3-{4-[3-Chloro-4-(6-methyl-pyridin-3-yloxy)-phenylamino]-quinazolin-6-yl}-prop-2-ynyl)-methanesulfonamide | B | 494.1 | 5.93 |

TABLE II

| Example No. | Name | method | mass spec | RT |
|---|---|---|---|---|
| 359 | Z-Cyclopropanecarboxylic acid (3-{4-[3-methyl-4-(6-methyl-pyridin-3-yloxy)-phenylamino]-quinazolin-6-yl}-allyl)-amide | J | 466.3 | 4.65 |
| 360 | Z-N-(3-{4-[3-Methyl-4-(6-methyl-pyridin-3-yloxy)-phenylamino]-quinazolin-6-yl}-allyl)-acetamide | J | 440.3 | 5.56 |
| 361 | Z-N-(3-{4-[3-Methyl-4-(6-methyl-pyridin-3-yloxy)-phenylamino]-quinazolin-6-yl}-allyl)-isobutyramide | J | 468.3 | 6.75 |

TABLE II-continued

| Example No. | Name | method | mass spec | RT |
|---|---|---|---|---|
| 362 | 3-{4-[3-Methyl-4-(6-methyl-pyridin-3-yloxy)-phenylamino]-quinazolin-6-yl}-prop-2-ynyl)-carbamic acid methyl ester | B | 454.3 | 5.93 |
| 363 | (3-{4-[3-Chloro-4-(6-methyl-pyridin-3-yloxy)-phenylamino]-quinazolin-6-yl}-prop-2-ynyl)-carbamic acid methyl ester | B | 474.2, 476.2 | 6.20 |
| 364 | 3-{4-[3-Chloro-4-(6-methyl-pyridin-3-yloxy)-phenylamino]-quinazolin-6-yl}-prop-2-ynyl)-carbamic acid tert-butyl ester | B | 517.3 | 7.34 |
| 365 | E-(3-{4-[3-Methyl-4-(6-methyl-pyridin-3-yloxy)-phenylamino]-quinazolin-6-yl}-allyl)-carbamic acid tert-butyl ester | G | 498.2 | 7.01 |
| 366 | 3-Methyl-pyridine-2-carboxylic acid (3-{4-[3-methyl-4-(6-methyl-pyridin-3-yloxy)-phenylamino]-quinazolin-6-yl}-allyl)-amide | G | 517.2 | 6.39 |
| 367 | E-N-(3-{4-[3-Chloro-4-(6-methyl-pyridin-3-yloxy)-phenylamino]-quinazolin-6-yl}-allyl)-benzenesulfonamide | G | 558.2 | 6.83 |
| 368 | 2-Fluoro-N-(3-{4-[3-methyl-4-(2-methyl-pyrimidin-5-yloxy)-phenylamino]-quinazolin-6-yl}-prop-2-ynyl)-acetamide | B | 457.2 | 4.92 |
| 369 | [3-Methyl-4-(2-methyl-pyrimidin-5-yloxy)-phenyl]-(6-piperidin-4-ylethynyl-quinazolin-4-yl)-amine | A | 451.5 | 4.09 |
| 370 | 2-Methoxy-N-(3-{4-[3-methyl-4-(2-methyl-pyrimidin-5-yloxy)-phenylamino]-quinazolin-6-yl}-prop-2-ynyl)-acetamide | B | 469.3 | 4.86 |
| 371 | E-2-Methoxy-N-(3-{4-[3-methyl-4-(2-methyl-pyrimidin-5-yloxy)-phenylamino]-quinazolin-6-yl}-allyl)-acetamide | G | 471.3 | 4.71 |
| 372 | 2-Methoxy-N-(3-{4-[3-methyl-4-(pyrimidin-5-yloxy)-phenylamino]-quinazolin-6-yl}-prop-2-ynyl)-acetamide | B | 455.4 | 4.79 |
| 373 | N-(3-{4-[3-Methyl-4-(pyrimidin-5-yloxy)-phenylamino]-quinazolin-6-yl}-prop-2-ynyl)-isobutyramide | B | 453.1 | 5.16 |
| 374 | 3-Methyl-isoxazole-5-carboxylic acid (3-{4-[3-methyl-4-(pyrimidin-5-yloxy)-phenylamino]-quinazolin-6-yl}-prop-2-ynyl)-amide | B | 492.1 | 5.27 |
| 375 | N-(3-{4-[3-Methyl-4-(pyrimidin-5-yloxy)-phenylamino]-quinazolin-6-yl}-prop-2-ynyl)-methanesulfonamide | B | 461.1 | 4.92 |
| 376 | (+)-[3-Methyl-4-(pyrimidin-5-yloxy)-phenyl]-(6-piperidin-3-ylethynyl-quinazolin-4-yl)-amine | A | 437.2 | 4.016 |
| 377 | 2-Methoxy-N-methyl-N-(3-{4-[3-methyl-4-(pyridin-3-yloxy)-phenylamino]-quinazolin-6-yl}-prop-2-ynyl)-acetamide | B | 468.3 | 5.52 |
| 378 | E-N-(3-{4-[3-Methyl-4-(pyridin-3-yloxy)-phenylamino]-quinazolin-6-yl}-allyl)-acetamide | G | 426.2 | 5.02 |
| 379 | E-2-Methoxy-N-(3-{4-[3-methyl-4-(pyridin-3-yloxy)-phenylamino]-quinazolin-6-yl}-allyl)-acetamide | G | 456.2 | 5.27 |
| 380 | E-(3-{4-[3-Methyl-4-(pyridin-3-yloxy)-phenylamino]-quinazolin-6-yl}-allyl)-carbamic acid methyl ester | G | 442.3 | 5.60 |
| 381 | E-N-(3-{4-[3-Methyl-4-(pyridin-3-yloxy)-phenylamino]-quinazolin-6-yl}-allyl)-methanesulfonamide | G | 462.0 | 5.29 |
| 382 | E-Cyclopropanecarboxylic acid (3-{4-[3-methyl-4-(pyridin-3-yloxy)-phenylamino]-quinazolin-6-yl}-allyl)-amide | G | 452.2 | 5.48 |
| 383 | E-Pyridine-2-carboxylic acid (3-{4-[3-methyl-4-(pyridin-3-yloxy)-phenylamino]-quinazolin-6-yl}-allyl)-amide | G | 489.1 | 6.15 |
| 384 | E-1-Ethyl-3-(3-{4-[3-methyl-4-(pyridin-3-yloxy)-phenylamino]-quinazolin-6-yl}-allyl)-urea | H | 455.3 | 5.16 |

Utilizing methods A through J and the appropriate starting materials (prepared according to methodology known in the art), the following compounds, which are part of the present invention, may be prepared:

Z-2-Methoxy-N-(3-{4-[3-methyl-4-(6-methyl-pyridin-3-yloxy)-phenylamino]-quinazolin-6-yl}-allyl)-acetamide E-2-(2-Fluoro-ethoxy)-N-(3-{4-[3-methyl-4-(6-methyl-pyridin-3-yloxy)-phenylamino]-quinazolin-6-yl}-allyl)-acetamide Z-N-(3-{4-[3-Chloro-4-(6-methyl-pyridin-3-yloxy)-phenylamino]-quinazolin-6-yl}-allyl)-2-fluoro-acetamide 2-Hydroxy-N-(1-{4-[3-methyl-4-(6-methyl-pyridin-3-yloxy)-phenylamino]-quinazolin-6-ylethynyl}-cyclopropyl)-acetamide E-2-Methoxy-N-(3-{4-[3-methyl-4-(6-methyl-pyridin-3-yloxy)-phenylamino]-quinazolin-6-yl}-allyl)-isobutyramide 1-Ethyl-3-(1-{4-[3-methyl-4-(6-methyl-pyridin-3-yloxy)-phenylamino]-quinazolin-6-ylethynyl}-cyclopropyl)-urea 1-Ethyl-3-[1-(2-{4-[3-methyl-4-(6-methyl-pyridin-3-yloxy)-phenylamino]-quinazolin-6-yl}-ethyl)-cyclopropyl]-urea 3-Methoxy-azetidine-1-carboxylic acid (3-{4-[3-methyl-4-(6-methyl-pyridin-3-yloxy)-phenylamino]-quinazolin-6-yl}-prop-2-ynyl)-amide N-(3-{7-(2-Methoxy-ethoxy)-4-[3-methyl-4-(6-methyl-pyridin-3-yloxy)-phenylamino]-quinazolin-6-yl}-prop-2-ynyl)-acetamide E-1-Methoxy-cyclopropanecarboxylic acid (3-{4-[3-methyl-4-(6-methyl-pyridin-3-yloxy)-phenylamino]-quinazolin-6-yl}-allyl)-amide N-(3-{4-[3-Methyl-4-(2-methyl-pyrimidin-5-yloxy)-phenylamino]-quinazolin-6-yl}-prop-2-ynyl)-acetamide (±)-E-1-(2-Fluoro-ethyl)-3-(1-methyl-3-{4-[3-methyl-4-(6-methyl-pyridin-3-yloxy)-phenylamino]-quinazolin-6-yl}-allyl)-urea E-N-[1-(2-{4-[3-Chloro-4-(6-methyl-pyridin-3-yloxy)-phenylamino]-quinazolin-6-yl}-vinyl)-cyclopropyl]-methanesulfonamide (±)-E-Tetrahydro-furan-3-carboxylic acid (3-{4-[3-chloro-4-(6-methyl-pyridin-3-yloxy)-phenylamino]-quinazolin-6-yl}-allyl)-amide E-Morpholine-4-carboxylic acid (3-{4-[3-methyl-4-(6-methyl-pyridin-3-yloxy)-phenylamino]-quinazolin-6-yl}-allyl)-amide N-[1-(2-{4-[3-Chloro-4-(6-methyl-pyridin-3-yloxy)-phenylamino]-quinazolin-6-yl}-ethyl)-cyclopropyl]-methanesulfonamide (±)-E-Tetrahydro-furan-2-carboxylic acid (3-{4-[3-chloro-4-(6-methyl-pyridin-3-yloxy)-phenylamino]-quinazolin-6-yl}-allyl)-amide (±)-Ethanesulfonic acid (1-methyl-3-{4-[3-methyl-4-(6-methyl-pyridin-3-yloxy)-phenylamino]-quinazolin-6-yl}-prop-2-ynyl)-amide (±)-Pyridine-2-carboxylic acid (1-methyl-3-{4-[3-methyl-4-(6-methyl-pyridin-3-yloxy)-phenylamino]-quinazolin-6-yl}-prop-2-ynyl)-amide and the pharmaceutically acceptable salts, solvates and prodrugs of the foregoing compounds.

The invention claimed is:
1. A compound of the formula 1

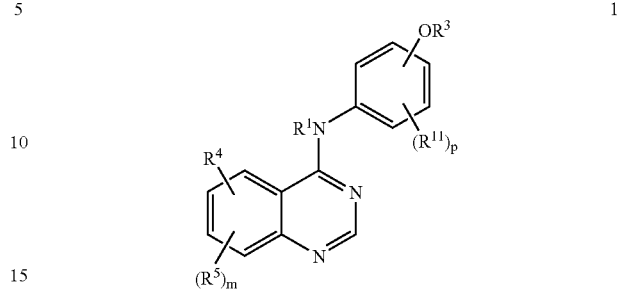

or a pharmaceutically acceptable salt or prodrug thereof, wherein:

m is an integer from 0 to 3;

p is an integer from 0 to 4;

each $R^1$ and $R^2$ is independently selected from H and $C_1$-$C_6$ alkyl;

$R^3$ is selected from

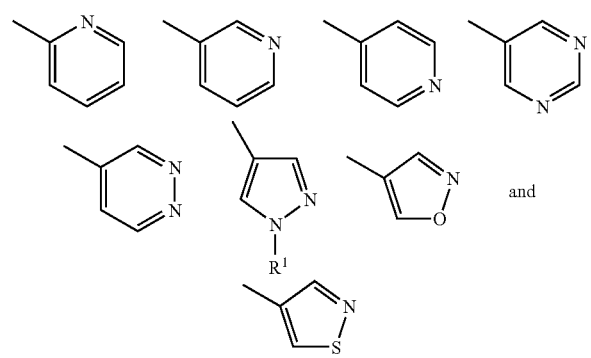

wherein the foregoing $R^3$ groups are optionally substituted by 1 to 3 $R^8$ groups;

$R^4$ is $-(CR^{16}R^{17})_m-C\equiv C-(CR^{16}R^{17})_t R^9$, $-CR^{16}R^{17})_m-C=C-(CR^{16}R^{17})_t-R^9$, or $-(CR^{16}R^{17})_t R^9$, wherein the attachment point to $R^9$ is through a carbon atom of the $R^9$ group, each t is an integer from 0 to 5, and each m is an integer from 0 to 3;

each $R^5$ is independently selected from halo, hydroxy, $-NR^1R^2$, $C_1$-$C_6$ alkyl, trifluoromethyl, $C_1$-$C_6$ alkoxy, trifluoromethoxy, $-NR^6C(O)R^1$, $-C(O)NR^6R^7$, $-SO_2NR^6R^7$, $-NR^6C(O)NR^7R^1$, and $-NR^6C(O)OR^7$;

each $R^6$ and $R^7$ is independently selected from H, $C_1$-$C_6$ alkyl, $-(CR^1R^2)_t(C_6$-$C_{10}$aryl), and $-(CR^1R^2)_t(4$ to 10 membered heterocyclic), wherein t is an integer from 0 to 5, 1 or 2 ring carbon atoms of the heterocyclic group are optionally substituted with an oxo (=O) moiety, the alkyl, aryl and heterocyclic moieties of the foregoing $R^6$ and $R^7$ groups are optionally substituted with 1 to 3 substituents independently selected from halo, cyano, nitro, $-NR^1R^2$, trifluoromethyl, trifluoromethoxy, $C_1$-$C_6$ alkyl, $C_2$-$C_6$ alkenyl, $C_2$-$C_6$ alkynyl, hydroxy, and $C_1$-$C_6$ alkoxy;

or $R^6$ and $R^7$, when attached to the same nitrogen atom, can be taken together to form a 4 to 10 membered heterocyclic ring which may include 1 to 3 additional hetero moieties, in addition to the nitrogen to which said $R^6$, and $R^7$ are attached, selected from N, $N(R^1)$, O, and S, provided two O atoms, two S atoms or an O and S atom are not attached directly to each other;

each $R^8$ is independently selected from oxo (=O), halo, cyano, nitro, trifluoromethoxy, trifluoromethyl, azido, hydroxy, $C_1$-$C_6$ alkoxy, $C_1$-$C_{10}$ alkyl, $C_2$-$C_6$ alkenyl, $C_2$-$C_6$ alkynyl, —C(O)$R^6$, —C(O)O$R^6$, —OC(O)$R^6$, —N$R^6$C(O)$R^7$, —N$R^6$SO$_2$N$R^7R^1$, —N$R^6$C(O)N$R^1R^7$, —N$R^6$C(O)O$R^7$, —C(O)N$R^6R^7$, —N$R^6R^7$, —N$R^6$O$R^7$, —SO$_2$N$R^6R^7$, —S(O)$_j$($C_1$-$C_6$ alkyl) wherein j is an integer from 0 to 2, —(C$R^1R^2$)$_t$($C_6$-$C_{10}$ aryl), —(C$R^1R^2$)$_t$(4 to 10 membered heterocyclic), —(C$R^1R^2$)$_q$C(O)(C$R^1R^2$)$_t$($C_6$-$C_{10}$ aryl), —(C$R^1R^2$)$_q$C(O)(C$R^1R^2$)$_t$(4 to 10 membered hetrocyclic), —(C$R^1R^2$)$_t$O(C$R^1R^2$)$_q$($C_6$-$C_{10}$ aryl), —(C$R^1R^2$)$_t$O(C$R^1R^2$)$_q$(4 to 10 membered hetrocyclic), —(C$R^1R^2$)$_q$S(O)$_j$(C$R^1R^2$)$_t$($C_6$-$C_{10}$ aryl), and —(C$R^1R^2$)$_q$S(O)$_j$(C$R^1R^2$)$_t$(4 to 10 membered heterocyclic), wherein j is 0, 1 or 2, q and t are each independently an integer from 0 to 5, 1 or 2 ring carbon atoms of the heterocyclic moieties of the foregoing $R^8$ groups are optionally substituted with an oxo (=O) moiety, and the alkyl, alkenyl, alkynyl, aryl and heterocyclic moieties of the foregoing $R^8$ groups are optionally substituted with 1 to 3 substituents independently selected from halo, cyano, nitro, trifluoromethyl, trifluoromethoxy, azido, —O$R^6$, —C(O)$R^6$, —C(O)O$R^6$, —OC(O)$R^6$, —N$R^6$C(O)$R^7$, —C(O)N$R^6R^7$, —N$R^6R^7$, —N$R^6$O$R^7$, $C_1$-$C_6$ alkyl, $C_2$-$C_6$ alkenyl, $C_2$-$C_6$ alkynyl, —(C$R^1R^2$)$_t$($C_6$-$C_{10}$ aryl), and —(C$R^1R^2$)$_t$(4 to 10 membered heterocyclic), wherein t is an integer from 0 to 5;

$R^9$ is a non-aromatic mono-cyclic ring, a fused or bridged bicyclic ring, or a spirocyclic ring, wherein said ring contains from 3 to 12 carbon atoms in which from 0 to 3 carbon atoms are optionally replaced with a hetero moiety independently selected from N, O, S(O)$_j$ wherein j is an integer from 0 to 2, and —N$R^1$—, provided that two O atoms, two S(O)$_j$ moieties, an O atom and a S(O)$_j$ moiety, an N atom and an S atom, or an N atom and an O atom are not attached directly to each other within said ring, and wherein the carbon atoms of said ring are optionally substituted with 1 or 2 $R^8$ groups;

each $R^{11}$ is independently selected from the substituents provided in the definition of $R^8$, except $R^{11}$ is not oxo(=O);

each $R^{16}$ and $R^{17}$ is independently selected from H, $C_1$-$C_6$ alkyl, and —CH$_2$OH, or $R^{16}$ and $R^{17}$ are taken together as —CH$_2$CH$_2$— or —CH$_2$CH$_2$CH$_2$—;

and wherein any of the above-mentioned substituents comprising a CH$_3$ (methyl), CH$_2$ (methylene), or CH (methine) group, which is not attached to a halogeno, SO or SO$_2$ group or to a N, O or S atom, is optionally subsituted with a group selected from hydroxy, halo, $C_1$-$C_4$ alkyl, $C_1$-$C_4$ alkoxy and —N$R^1R^2$.

2. A compound according to claim 1 wherein $R^3$ is pyridin-3-yl optionally substituted by 1 to 3 $R^8$ groups.

3. A compound according to claim 1 wherein the following structural portion of the compound of formula 1

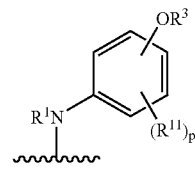

is selected from the group consisting of
3-Methyl-4-(pyridin-2-yloxy)-phenylamino
3-Chloro-4-(pyridin-2-yloxy)-phenylamino
3-Methoxy-4-(pyridin-2-yloxy)-phenylamino
4-(pyridin-2-yloxy)-phenylamino
2-Methyl-4-(pyridin-2-yloxy)-phenylamino
2-Methoxy-4-(pyridin-2-yloxy)-phenylamino
3-Chloro-4-(6-methyl-pyridin-2-yloxy)-phenylamino
3-Methoxy-4-(6-methyl-pyridin-2-yloxy)-phenylamino
3-Methyl-4-(6-methyl-pyridin-2-yloxy)-phenylamino
2-Methoxy-4-(6-methyl-pyridin-2-yloxy)-phenylamino
2-Methyl-4-(6-methyl-pyridin-2-yloxy)-phenylamino
4-(6-methyl-pyridin-2-yloxy)-phenylamino
3-Methoxy-4-(2-methyl-pyridin-3-yloxy)-phenylamino
3-Methyl-4-(2-methyl-pyridin-3-yloxy)- phenylamino
3-Chloro-4-(2-methyl-pyridin-3-yloxy)-phenylamino
2-Methoxy-4-(2-methyl-pyridin-3-yloxy)-phenylamino
2-Methyl-4-(2-methyl-pyridin-3-yloxy)-phenylamino
4-(2-methyl-pyridin-3-yloxy)-phenylamino
3- Methyl-4-(6-methyl-pyridin-3-yloxy)-phenylamino
3-Chloro-4-(6-methyl-pyridin-3-yloxy)-phenylamino
3-Methoxy-4-(6-methyl-pyridin-3-yloxy)-phenylamino
2-Methyl-4-(6-methyl-pyridin-3-yloxy)-phenylamino
2-Methoxy-4-(6-methyl-pyridin-3-yloxy)-phenylamino
4-(6-methyl-pyridin-3-yloxy)-phenylamino
3-Methyl-4-(pyridin-3-yloxy)-phenylamino
3-Chloro-4-(pyridin-3-yloxy)-phenylamino
3-Methoxy-4-(pyridin-3-yloxy)-phenylamino
2-Methyl-4-(pyridin-3-yloxy)-phenylamino
2-Methoxy-4-(pyridin-3-yloxy)-phenylamino
4-(pyridin-3-yloxy)-phenylamino
3-Methyl-4-(2-methyl-pyrimidin-5-yloxy)-phenylamino
3-Chloro-4-(2-methyl-pyrimidin-5-yloxy)-phenylamino
3-Methoxy-4-(2-methyl-pyrimidin-5-yloxy)-phenylamino
2-Methyl-4-(2-methyl-pyrimidin-5-yloxy)-phenylamino
2-Methoxy-4-(2-methyl-pyrimidin-5-yloxy)-phenylamino
4-(2-methyl-pyrimidin-5-yloxy)-phenylamino
3-Methyl-4-(4-methyl-pyrimidin-5-yloxy)-phenylamino
3-Chloro-4-(4-methyl-pyrimidin-5-yloxy)-phenylamino
3-Methoxy-4-(4-methyl-pyrimidin-5-yloxy)-phenylamino
2-Methyl-4-(4-methyl-pyrimidin-5-yloxy)-phenylamino
2-Methoxy-4-(4-methyl-pyrimidin-5-yloxy)-phenylamino
4-(4-methyl-pyrimidin-5-yloxy)-phenylamino
3-Methyl-4-(2-methyl-pyridin-4-yloxy)-phenylamino
3-Chloro-4-(2-methyl-pyridin-4-yloxy)-phenylamino
3-Methoxy-4-(2-methyl-pyridin-4-yloxy)-phenylamino
2-Methyl-4-(2-methyl-pyridin-4-yloxy)-phenylamino
2-Methoxy-4-(2-methyl-pyridin-4-yloxy)-phenylamino
4-(2-methyl-pyridin-4-yloxy)-phenylamino
3-Methyl-4-(pyridin-4-yloxy)-phenylamino
3-Chloro-4-(pyridin-4-yloxy)-phenylamino
3-Methoxy-4-(pyridin-4-yloxy)-phenylamino
2-Methyl-4-(pyridin-4-yloxy)-phenylamino 2-Methoxy-4-(pyridin-4-yloxy)-phenylamino
4-(pyridin-4-yloxy)-phenylamino
3-Methyl-4-(2-methyl-pyridin-4-yloxy)-phenylamino
3-Methoxy-4-(2-methyl-pyrimidin-4-yloxy)-phenylamino
3-Chloro-4-(2-methyl-pyrimidin-4-yloxy)-phenylamino
2-Methyl-4-(2-methyl-pyrimidin-4-yloxy)-phenylamino
2-Methoxy-4-(2-methyl-pyrimidin-4-yloxy)-phenylamino
4-(2-methyl-pyrimidin-4-yloxy)-phenylamino
3-Methyl-4-(6-methyl-pyrimidin-4-yloxy)-phenylamino
3-Methoxy-4-(6-methyl-pyrimidin-4-yloxy)-phenylamino
3-Chloro-4-(6-methyl-pyrimidin-4-yloxy)-phenylamino
2-Methyl-4-(6-methyl-pyrimidin-4-yloxy)-phenylamino
2-Methoxy-4-(6-methyl-pyrimidin-4-yloxy)-phenylamino
4-(6-methyl-pyrimidin-4-yloxy)-phenylamino
3-Methyl-4-(pyridazin-3-yloxy)-phenylamino
3-Chloro-4-(pyridazin-3-yloxy)-phenylamino
3-Methoxy-4-(pyridazin-3-yloxy)-phenylamino
2-Methyl-4-(pyridazin-3-yloxy)-phenylamino
2-Methoxy-4-(pyridazin-3-yloxy)-phenylamino
4-(pyridazin-3-yloxy)-phenylamino
3-Methyl-4-(6-methyl-pyridazin-3-yloxy)-phenylamino
3-Chloro-4-(6-methyl-pyridazin-3-yloxy)-phenylamino
3-Methoxy-4-(6-methyl-pyridazin-3-yloxy)-phenylamino
2-Methyl-4-(6-methyl-pyridazin-3-yloxy)-phenylamino
2-Methoxy-4-(6-methyl-pyridazin-3-yloxy)-phenylamino
4-(6-methyl-pyridazin-3-yloxy)-phenylamino
3-Methyl-4-(6-methyl-pyridazin-4-yloxy)-phenylamino
3-Chloro-4-(6-methyl-pyridazin-4-yloxy)-phenylamino
3-Methoxy-4-(6-methyl-pyridazin-4-yloxy)-phenylamino
2-Methyl-4-(6-methyl-pyridazin-4-yloxy)-phenylamino
2-Methoxy-4-(6-methyl-pyridazin-4-yloxy)-phenylamino
4-(6-methyl-pyridazin-4-yloxy)-phenylamino
3-Methyl-4-(3-methyl-pyridazin-4-yloxy)-phenylamino
3-Chloro-4-(3-methyl-pyridazin-4-yloxy)-phenylamino
3-Methoxy-4-(3-methyl-pyridazin-4-yloxy)-phenylamino
2-Methyl-4-(3-methyl-pyridazin-4-yloxy)-phenylamino
2-Methoxy-4-(3-methyl-pyridazin-4-yloxy)-phenylamino
4-(3-methyl-pyridazin-4-yloxy)-phenylamino
3-Methyl-4-(pyridazin-4-yloxy)-phenylamino
3-Chloro-4-(pyridazin-4-yloxy)-phenylamino
3-Methoxy-4-(pyridazin-4-yloxy)-phenylamino
2-Methyl-4-(pyridazin-4-yloxy)-phenylamino
2-Methoxy-4-(pyridazin-4-yloxy)-phenylamino
4-(pyridazin-4-yloxy)-phenylamino
3-Chloro-4-(1-methyl-1H-pyrazol-4-yloxy)-phenylamino
3-Methoxy-4-(1-methyl-1H-pyrazol-4-yloxy)-phenylamino
3-Methyl-4-(1-methyl-1H-pyrazol-4-yloxy)-phenylamino
2-Methoxy-4-(1-methyl-1H-pyrazol-4-yloxy)-phenylamino
2-Methyl-4-(1-methyl-1H-pyrazol-4-yloxy)-phenylamino, and
4-(1-methyl-1H-pyrazol-4-yloxy)-phenylamino.

4. A compound according to claim 1 wherein $R^4$ is —$(CR^{16}R^{17})_m$—C≡C—$(CR^{16}R^{17})_t R^9$, wherein m is an integer from 0 to 3, and t is an integer from 0 to 5.

5. A compound according to claim 1 wherein $R^4$ is —$(CR^{16}R^{17})_m$—C≡C—$(CR^{16}R^{17})_t R^9$, wherein m is an integer from 0 to 3, and t is an integer from 0 to 5, wherein $R^9$ is selected from 3-piperidinyl and 4-piperidinyl each of which is optionally substituted with 1 or 2 $R^8$ groups.

6. A compound according to claim 1 wherein $R^4$ is, —$(CR^{16}R^{17})_m$—C≡C—$(CR^{16}R^{17})_t$—$R^9$, wherein m is an integer from 0 to 3, and t is an integer from 0 to 5.

7. A compound according to claim 1 wherein $R^4$ is, —$(CR^{16}R^{17})_m$—C≡C—$(CR^{16}R^{17})_t$—$R^9$, wherein m is an integer from 0 to 3, and t is an integer from 0 to 5, wherein $R^9$ is selected from 3-piperidinyl and 4-piperidinyl (optionally substituted with 1 or 2 $R^8$ groups).

8. A compound according to claim 1 selected from the group consisting of:
   (±)-[3-Methyl-4-(pyridin-3-yloxy)-phenyl]-(6-piperidin-3-ylethynyl-quinazolin-4-yl)-amine;
   (±)-[3-Methyl-4-(6-methyl-pyridin-3-yloxy)-phenyl]-(6-piperidin-3-ylethynyl-quinazolin-4(yl)-amine;
   [3-Methyl-4-(2-methyl-pyridin-3-yloxy)-phenyl]-(6-piperidin-4-ylethynyl-quinazolin-4-yl)-amine
   [3-Methyl-4-(6-methyl-pyridin-3-yloxy)-phenyl]-(6-piperidin-4-ylethynyl-quinazolin-4-yl)-amine
   and the pharmaceutically acceptable salts, prodrugs of the foregoing compounds.

9. A pharmaceutical composition for the treatment of abnormal cell growth in a mammal comprising an amount of a compound of claim 1 that is effective in treating abnormal cell growth, and a pharmaceutically acceptable carrier.

10. A compound according to claim 1 wherein $R^4$ is —$(CR^{16}R^{17})_t R^9$ wherein t is an integer from 0 to 5.

11. A compound according to claim 10, wherein t is 0.

* * * * *